United States Patent [19]

Takematsu et al.

[11] Patent Number: 4,932,998

[45] Date of Patent: Jun. 12, 1990

[54] TRIAZINE DERIVATIVES, AND HERBICIDES COMPRISING THE SAME AS THE EFFECTIVE INGREDIENT

[75] Inventors: Tetsuo Takematsu, Utsunomiya; Masahiro Nishii; Izumi Kobayashi, both of Sodegaura, all of Japan

[73] Assignee: Idemitsu Kosan Company Limited, Tokyo, Japan

[21] Appl. No.: 328,019

[22] Filed: Mar. 23, 1989

Related U.S. Application Data

[63] Continuation-in-part of Ser. No. 183,731, filed as PCT JP87/00710 on Sep. 29, 1987, published as WO88/02368 on Apr. 7, 1988, abandoned.

[30] Foreign Application Priority Data

Sep. 30, 1986 [JP] Japan .................................. 61-229781
Mar. 29, 1988 [JP] Japan .................................... 63-73143

[51] Int. Cl.$^5$ ................... A01N 43/68; C07D 251/18; C07D 409/12; C07D 407/12
[52] U.S. Cl. ............................................. 71/90; 71/93; 544/207

[58] Field of Search ........................ 544/207; 71/93, 90

[56] References Cited

U.S. PATENT DOCUMENTS 3,162,633 12/1964 Shaw .................................... 544/207

Primary Examiner—John M. Ford
Attorney, Agent, or Firm—Frishauf, Holtz, Goodman & Woodward

[57] ABSTRACT

The triazine derivatives of the present invention are roughly classified into the compounds of the general formulas [I] and [II] and further classified into 4 types depending on the kind of the Z in the general formulas and the position of substitution of the aminoalkyl group on the benzo(thia)furanyl group. Furthermore, these triazine derivatives are useful as a herbicide or, in particular, as a herbicide for paddy rice plants with greater effectiveness and less injury by chemicals than known ones. In addition, they have a wide herbicidal spectrum and exhibit remarkable effects against various kinds of weeds.

43 Claims, No Drawings

TRIAZINE DERIVATIVES, AND HERBICIDES COMPRISING THE SAME AS THE EFFECTIVE INGREDIENT

This application is a continuation-in-part of U.S. Ser. No. 07/183,731 filed as PCT JP87/00710 on Sep. 29, 1987, published as WO88/02368 on Apr. 7, 1988, now abandoned.

FIELD OF TECHNOLOGY

The present invention relates to a novel triazine derivative, and a herbicide containing the same as the effective ingredient.

BACKGROUND TECHNOLOGY

Known triazine-based herbicides include those comprising 2-amino-4-(α-methyl benzyl amino)-6-trifluoromethyl-s-triazine and the like having a triazine ring substituted with a haloalkyl group as the effective ingredient.

These compounds, however, cannot exhibit full herbicidal effects when they are applied to paddy rice plants and, in addition, they have a disadvantage of bad phytotoxicity against paddy rice plants.

The first of the objects of the present invention is to provide a herbicide which is free from the phytotoxicity against paddy rice plants and exhibits excellent herbicidal effects against various kinds of weeds including annual weeds and perennial weeds with good persistence. The object is also to provide a herbicide safely applicable to upland crops of the Grass family such as corn, wheat, barley and the like.

The second of the objects of the present invention is to provide a novel triazine derivative useful as an effective ingredient in the above mentioned herbicide.

DISCLOSURE OF THE INVENTION

The present invention provides:

(1) a triazine derivative represented by the general formula

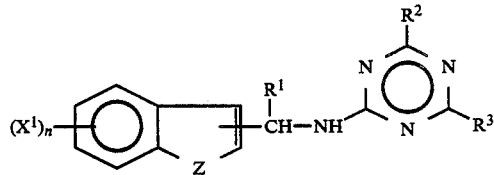

or by the general formula

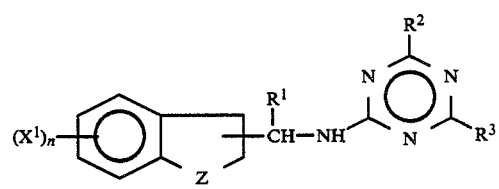

[in the formulas, $X^1$ is a hydrogen atom, alkyl group having 1 to 4 carbon atoms, alkoxy group having 1 to 4 carbon atoms, alkylthio group having 1 to 4 carbon atoms, halogen atom, halogen-substituted alkyl group having 1 to 4 carbon atoms, halogen-substituted alkoxy group having 1 to 4 carbon atoms, halogen-substituted alkylthio group having 1 to 4 carbon atoms, n is an integer of 1 to 4, Z is an oxygen atom or sulfur atom, $R^1$ is an alkyl group having 1 to 4 carbon atoms, $R^2$ is a halogen-substituted alkyl group having 1 to 4 carbon atoms and $R^3$ is $NH_2$, $NHCOR^4$ or $N=CHR^5$ (in which $R^4$ is a hydrogen atom, alkyl group having 1 to 4 carbon atoms, cycloalkyl group having 3 to 6 carbon atoms of alkenyl group having 2 to 5 carbon atoms and $R^5$ is an alkyl group having 1 to 4 carbon atoms, alkoxy group having 1 to 4 carbon atoms or alkylamino group having 1 to 4 carbon atoms)];

(2) a herbicide containing, as an effective ingredient, a triazine derivative represented by the general formula

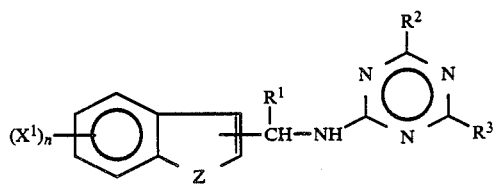

or by the general formula

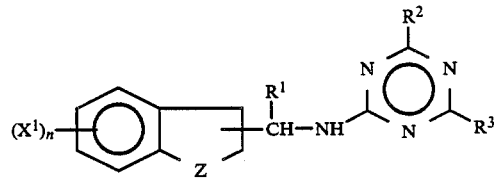

[in the formulas, $X^1$ is a hydrogen atom, alkyl group having 1 to 4 carbon atoms, alkoxy group having 1 to 4 carbon atoms, alkylthio group having 1 to 4 carbon atoms, halogen atom, halogen-substituted alkyl group having 1 to 4 carbon atoms, halogen-substituted alkoxy group having 1 to 4 carbon atoms or halogen-substituted alkylthio group having 1 to 4 carbon atoms, n is an integer of 1 to 4, Z is an oxygen atom or a sulfur atom, $R^1$ is an alkyl group having 1 to 4 carbon atoms, $R^2$ is a halogen-substituted alkyl group having 1 to 4 carbon atoms and $R^3$ is $NH_2$, $NHCOR^4$ or $N=CHR^5$ (in which $R^4$ is a hydrogen atom, alkyl group having 1 to 4 carbon atoms, substituted alkyl group having 1 to 4 carbon atoms, cycloalkyl group having 3 to 6 carbon atoms or alkenyl group having 2 to 5 carbon atoms and $R^5$ is an alkyl group having 1 to 4 carbon atoms, alkoxy group having 1 to 4 carbon atoms or alkylamino group having 1 to 4 carbon atoms)].

The triazine derivative of the present invention is a novel compound and can be utilized efficiently as a herbicide.

Besides, the herbicide of the present invention comprising the above mentioned triazine derivative as an active ingredient has a high herbicidal effect and low phytotoxicity in comparison with known herbicides for paddy rice plants. Moreover, it has a broad herbicidal spectrum and exhibits strong effects against various kinds of weeds.

BEST EMBODIMENT FOR PRACTICING THE INVENTION

The present invention provides a triazine derivative represented by the general formula

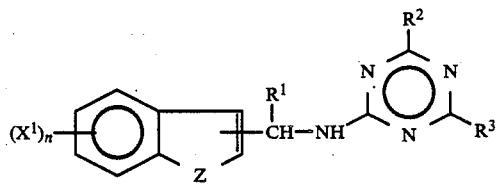

or by the general formula

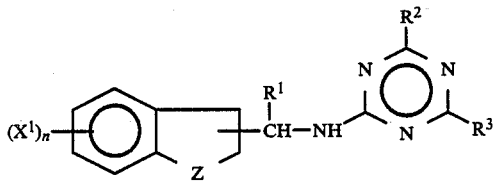

[in the formulas, $X^1$ is a hydrogen atom, alkyl group having 1 to 4 carbon atoms, alkoxy group having 1 to 4 carbon atoms, alkylthio group having 1 to 4 carbon atoms, halogen atom, halogen-substituted alkyl group having 1 to 4 carbon atoms, halogen-substituted alkoxy group having 1 to 4 carbon atoms or halogen-substituted alkylthio group having 1 to 4 carbon atoms, n is an integer of 1 to 4, Z is an oxygen atom or a sulfur atom, $R^1$ is an alkyl group having 1 to 4 carbon atoms, $R^2$ is a halogen-substituted alkyl group having 1 to 4 carbon atoms and $R^3$ is $NH_2$, $NHCOR^4$ or $N=CHR^5$ (in which $R^4$ is a hydrogen atom, alkyl group having 1 to 4 carbon atoms, substituted alkyl group having 1 to 4 carbon atoms, cycloalkyl group having 3 to 6 carbon atoms or alkenyl group having 2 to 5 carbon atoms, and $R^5$ is an alkyl group having 1 to 4 carbon atoms, alkoxy group having 1 to 4 carbon atoms or alkyl amino group having 1 to 4 carbon atoms)] and also provides a triazine derivative represented by the general formula

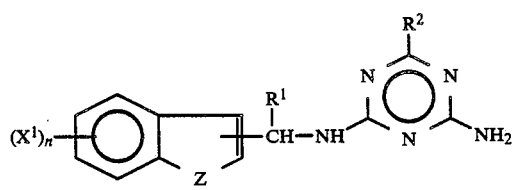

[in the formula, $X^1$, n, Z, $R^1$ and $R^2$ each have the same meaning as above] characterized by reacting a salt of benzofuranyl alkyl amine represented by the general formula

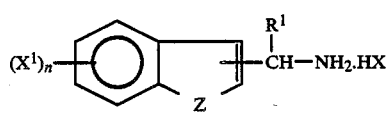

[in the formula, $X^1$, n, Z and $R^1$ each have the same meaning as above and X is a halogen atom] with a cyanoguanidine expressed by the formula

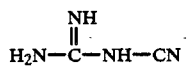

to prepare a salt of a benzofuranyl biguanide represented by the general formula

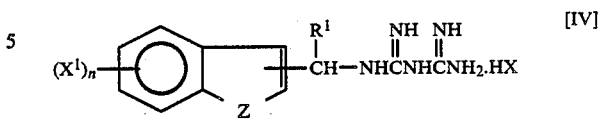

[in the formula, $X^1$, n, Z, $R^1$ and X each have the same meaning as above] and then reacting the salt of benzofuranyl biguanide with an alkyl ester represented by the general formula $R^2COOR^6$  [V]

[in the formula, $R^2$ is a halogen-substituted alkyl group having 1 to 4 carbon atoms and $R^6$ is an alkyl group having 1 to 4 carbon atoms] (hereinafter referred to as "the method 1") and a method for the preparation of a triazine derivative represented by the general formula

[in the formula, $X^1$, n, Z, $R^1$ and $R^2$ each have the same meaning as above] characterized by reacting a salt of a dihydrobenzofuranyl alkyl amine represented by the general formula

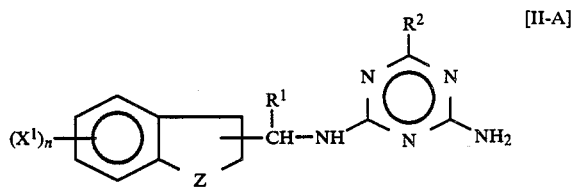

[in the formula, $X^1$, n, Z and $R^1$ each have the same meaning as above and X is a halogen atom] with cyanoguanidine expressed by the formula

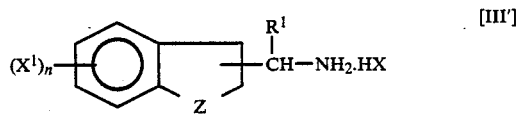

to prepare a salt of dihydrobenzofuranyl biguanide represented by the general formula

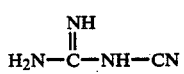

[in the formula, $X^1$, n, Z, $R^1$ and X each have the same meaning as above] and then reacting the salt of dihydrobenzofuranyl biguanide with an alkyl ester represented by the above given general formula [V] (hereinafter referred to as "the method 2").

Further, the present invention also provides a method for the preparation of a compound which is the triazine derivative of the general formula [I] or [II] having $NHCOR^4$ or $N=CHR^5$ as the substituent group $R^3$ as an extension of the above described method 1 or method 2.

Namely, there are provided a method for the preparation of a triazine derivative represented by the general formula

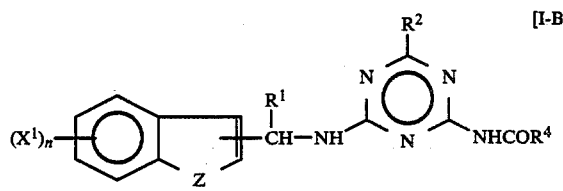

[in the formula, $X^1$, n, Z, $R^1$, $R^2$ and $R^4$ each have the same meaning as above] (hereinafter referred to as "the method 3") by reacting the triazine derivative (amino group-containing triazine derivative) represented by the general formula [I-A] and prepared by the above described method 1 with a carboxylic acid represented by the general formula

$R^4COOH$ [VI]

[in the formula, $R^4$ has the same meaning as above], a carboxylic acid anhydride represented by the general formula

$(R^4CO)_2O$ [VII]

[in the formula, $R^4$ has the same meaning as above], a halide of carboxylic acid represented by the general formula

$R^4COX$ [VIII]

[in the formula, $R^4$ and X each have the same meaning as above] or an ester of carboxylic acid represented by the general formula

$R^4COOR^7$ [IX]

[in the formula, $R^4$ has the same meaning as above and $R^7$ is an alkyl group having 1 to 4 carbon atoms] and a method for the preparation of a triazine derivative represented by the general formula

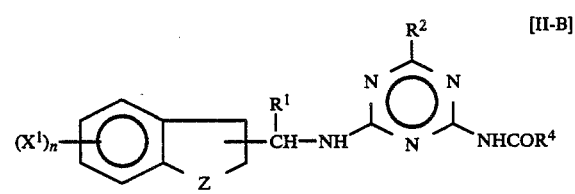

[in the formula, $X^1$, n, Z, $R^1$, $R^2$ and $R^4$ each have the same meaning as above] (hereinafter referred to as "the method 4") by reacting the triazine derivative (amino group-containing triazine derivative) represented by the general formula [II-A] and prepared by the above described method 2 with a carboxylic acid of the above given general formula [VI], carboxylic acid anhydride of the general formula [VII], halide of carboxylic acid of the general formula [VIII] or ester of carboxylic acid of the general formula [IX] and further there are provided a method for the preparation of a triazine derivative represented by the general formula

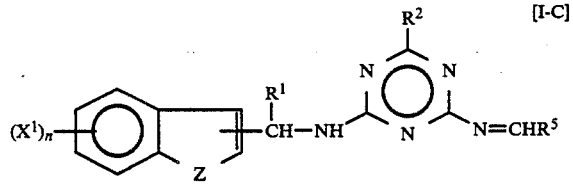

[in the formula, $X^1$, n, Z, $R^1$, $R^2$ and $R^5$ each have the same meaning as above] (hereinafter referred to as "the method 5") by reacting the amino group-containing triazine derivative represented by the general formula [I-A] and prepared by the above described method 1 with an aldehyde represented by the general formula

$R^5CHO$ [X]

[in the formula, $R^5$ has the same meaning as above] or an acetal represented by the general formula

$R^5CH(OR^8)_2$ [XI]

[in the formula, $R^5$ has the same meaning as above and $R^8$ is an alkyl group having 1 to 4 carbon atoms] and a method for the preparation of a triazine derivative represented by the general formula

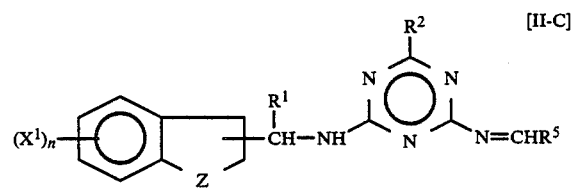

[in the formula, $X^1$, n, Z, $R^1$, $R^2$ and $R^5$ each have the same meaning as above] (hereinafter referred to as "the method 6") by reacting the amino group-containing triazine derivative represented by the general formula [II-A] and prepared by the above described method 2 with an aldehyde of the above given general formula [X] or an acetal of the general formula [XI].

Further, the present invention provides a herbicide containing, as an effective ingredient, the triazine derivative represented by the above given general formula [I] (this includes the general formulas [I-A], [I-B] and [I-C]) or the general formula [II] (this includes the general formulas [II-A], [II-B] and [II-C]).

The compound represented by the above given general formula [I] is a triazine derivative (triazine derivative having a benzo(thia)furanyl group) and, in the formula, $X^1$, n, Z, $R^1$, $R^2$ and $R^3$ are each as described above. Namely, $X^1$ denotes a hydrogen atom, alkyl group having 1 to 4 carbon atoms (methyl group, ethyl group, n-propyl group, isopropyl group, n-butyl group, isobutyl group, sec-butyl group and tert-butyl group), alkoxy group having 1 to 4 carbon atoms (methoxy group, ethoxy group, n-propoxy group, isopropoxy group, n-butoxy group, isobutoxy group, sec-butoxy group and tert-butoxy group), alkylthio group having 1 to 4 carbon atoms (methylthio group, ethylthio group, propylthio group and butylthio group), halogen atom (chlorine atom, bromine atom, fluorine atom, iodine atom and the like), halogen-substituted alkyl group having 1 to 4 carbon atoms (trifluoromethyl group, trichloromethyl group, trichloroethyl group, dichloroethyl group, tetrafluoroethyl group, monochloromethyl group, monobromomethyl group, monofluoromethyl group and the like), halogen-substituted alkoxy group having 1 to 4 carbon atoms (monochloromethoxy group, difluoromethoxy group, monochloroethoxy group, monofluoromethoxy group, trifluoromethoxy group and the like) or halogen-substituted alkylthio group (monochloromethylthio group, difluoromethylthio group, monochloroethylthio group, monofluoromethylthio group and trifluoromethylthio group). And, n denotes either one of the integers of 1 to 4 and Z denotes an oxygen atom or a sulfur atom. Further, $R^1$ is an alkyl group having 1 to 4 carbon atoms such as methyl group, ethyl group, n-propyl group, isopropyl group, n-butyl group, isobutyl group, sec-butyl group and tert-butyl group and $R^2$ is a haolgen-substituted alkyl group having 1 to 4 carbon atoms such as, in particular, trifluoromethyl group, trichloromethyl group, dichloroethyl group, tetrafluoroethyl group, monochloromethyl group, monobromomethyl group, monofluoromethyl group, difluoromethyl group, chlorofluoromethyl group, dibromoethyl group, dichloromethyl group, bromofluoromethyl group, heptafluoropropyl group, dibromomethyl group, dibromofluoromethyl group, chlorodifluoromethyl group, bromodifluoromethyl group, dichlorofluoromethyl group, pentafluoroethyl group, difluoroethyl group and the like. And, $R^3$ is $NH_2$, $NHCOR^4$ or $N=CHR^5$. $R^4$ here is a hydrogen atom, alkyl group having 1 to 4 carbon atoms, substituted alkyl group having 1 to 4 carbon atoms, cycloalkyl group having 3 to 6 carbon atoms or alkenyl group having 2 to 5 carbon atoms exemplified, in particular, by methyl group, ethyl group, n-propyl group, isopropyl group, n-butyl group, isobutyl group, sec-butyl group, tert-butyl group, methoxy methyl group, methoxy ethyl group, ethoxy methyl group, chloromethyl group, dichloromethyl group, bromomethyl group, methylthio methyl group, ethylthio methyl group, cyclopropyl group, cyclobutyl group, cyclopentyl group, cyclohexyl group, vinyl group, propenyl group, allyl group and the like. Further, $R^5$ is an alkyl group having 1 to 4 carbon atoms, alkoxy group having 1 to 4 carbon atoms or alkyl amino group having 1 to 4 carbon atoms exemplified, in particular, by methyl group, ethyl group, n-propyl group, isopropyl group, n-butyl group, isobutyl group, sec-butyl group, tert-butyl group, methoxy group, ethoxy group, n-propoxy group, isopropoxy group, n-butoxy group, isobutoxy group, sec-butoxy group, tert-butoxy group, monomethyl amino group, dimethyl amino group, monoethyl amino group, diethyl amino group and the like.

The triazine derivatives represented by the general formula [I] can be classified into 4 classes shown below depending on the kind of Z in the formula and the position of substitution of the aminoalkyl group [—CHR$^1$—NH] to the benzo(thia)furanyl group. Namely, an oxygen atom as the Z gives the triazine derivatives (triazine derivatives having a 2-benzofuranyl group) represented by the general formula

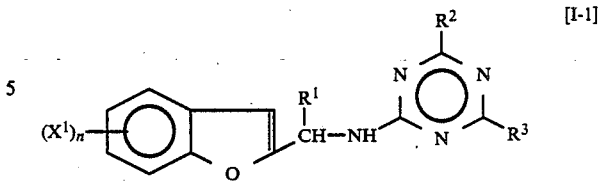

or triazine derivatives (triazine derivatives having a 3-benzofuranyl group) represented by the general formula

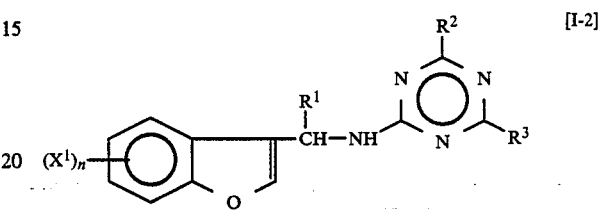

and a sulfur atom as the Z gives triazine derivatives (triazine derivatives having a 2-benzothiafuranyl group (2-benzothienyl group or 2-thianaphthenyl group)) represented by the general formula

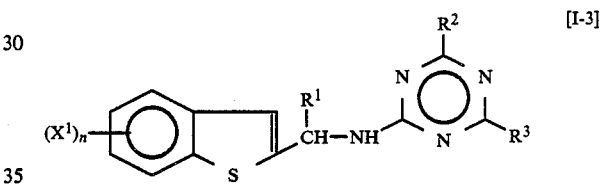

or triazine derivatives (triazine derivatives having a 3-benzothiafuranyl group (3-benzothienyl group or 3-thianaphthenyl group)) represented by the general formula

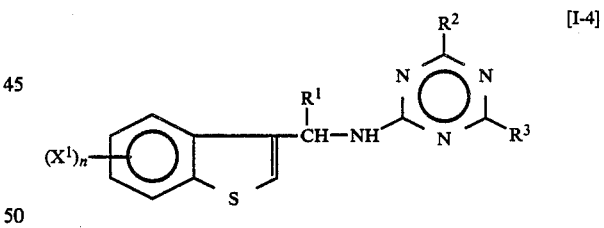

On the other hand, the compound represented by the general formula [II] is also a triazine derivative (triazine derivative having a dihydrobenzo(thia)furanyl group) which is the same as the triazine derivative of the general formula [I] excepting saturation or unsaturation of the carbon atoms at the 2,3-positions of the benzo(thia)furanyl group with hydrogen atoms so that the particular examples of $X^1$, n, Z, $R^1$, $R^2$ and $R^3$ are the same as in the case of the triazine derivatives of the general formula.

Similarly to the triazine derivatives of the above given general formula [I], the triazine derivatives represented by the general formula [II] can also be classified into the following 4 classes depending on the kind of the Z in the formula and the position of substitution of the aminoalkyl group [—CHR$^1$—NH] to the benzo(thia)furanyl group.

Namely, an oxygen atom as the Z gives triazine derivatives (triazine derivatives having a 2-dihydrobenzofuranyl group) represented by the general formula

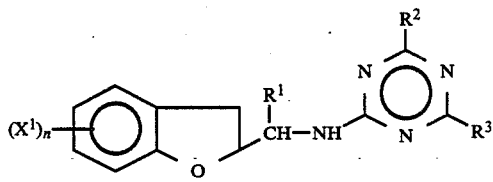

or triazine derivatives (triazine derivatives having a 3-dihydrobenzofuranyl group) represented by the general formula

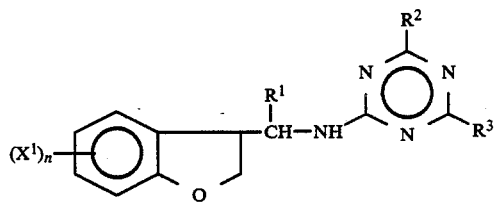

and a sulfur atom as the Z gives triazine derivatives (triazine derivatives having a 2-dihydrobenzothiafuranyl group (2-dihydrobenzothienyl group or 2-dihydrothianaphthenyl group)) represented by the general formula

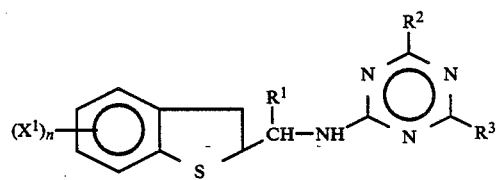

or triazine derivatives (triazine derivatives having a 3-dihydrobenzothiafuranyl group (3-dihydrobenzothienyl group or 3-dihydrothianaphthenyl group)) represented by the general formula

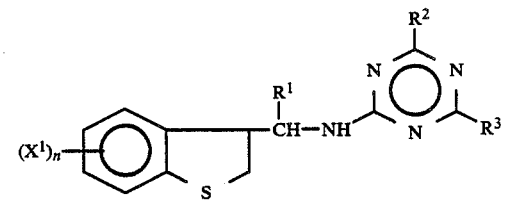

Particularly exemplary of the triazine derivatives of the present invention represented by the above given general formulas [I-1] to [I-4] and [II1] to [II-4] are, besides the compounds obtained in the Preparation Examples described below, 2-amino-4-[1-(benzofuran-2'-yl) ethylamino]-6-dichloromethyl-s-triazine, 2-amino-4-[1-(benzofuran-2'-yl) ethylamino]-6-dibromomethyl-s-triazine, 2-amino-4-[1-(benzofuran-2'-yl) ethylamino]-6-trichloromethyl-s-triazine, 2-amino-4-[1-(benzofuran-2'-yl) ethylamino]-dichlorofluoromethyl-s-triazine, 2-amino-4-[1-(benzofuran-2'-yl) ethylamino]-6-chlorofluoromethyl-s-triazine, 2-amino-4-[1-(benzofuran-2'-yl) ethylamino]-6-bromofluoromethyl-s-triazine, 2-amino-4-[1-(benzofuran-2'-yl) ethylamino]-6-dibromofluoromethyl-s-triazine, 2-amino-4-[1-(benzofuran-2'-yl) ethylamino]-6-bromodifluoromethyl-s-triazine, 2-amino-4-[1-(benzofuran-2'-yl) ethylamino]-6-bromomethyl-s-triazine, 2-amino-4-[1-(benzofuran-2'-yl) ethylamino]-6-chloromethyl-s-triazine, 2-amino-4-[1-(benzofuran-2'-yl) ethylamino]-6-$\alpha,\beta$-dibromoethyl-s-triazine, 2-amino-4-[1-(benzofuran-2'-yl) ethylamino]-6-pentafluoroethyl-s-triazine, 2-amino-4-[1-(benzofuran-2'-yl) ethylamino]-6-$\alpha,\alpha$-difluoroethyl-s-triazine, 2-amino-4-[1-(benzofuran-2'-yl) ethylamino]-6-heptafluoropropyl-s-triazine, 2-amino-4-[1-(thianaphthen-2'-yl) ethylamino]-6-trifluoromethyl-s-triazine, 2-amino-4-[1-(thianaphthen-2'-yl) ethylamino]-6-$\alpha,\alpha$-dichloroethyl-s-triazine, 2-amino-4-[1-(thianaphthen-2'-yl) ethylamino]-6-$\alpha,\alpha,\beta,\beta$-tetrafluoromethyl-s-triazine, 2-amino-4-[1-(thianaphthen-2'-yl) ethylamino]-6-monofluoromethyl-s-triazine, 2-amino-4-[1-(thianaphthen-2'-yl) ethylamino]-6-trichloromethyl-s-triazine, 2-amino-4-[1-(thianaphthen-3'-yl) ethylamino]-6-$\alpha,\alpha$-dichloroethyl-s-triazine, 2-amino-4-[1-(thianaphthen-3'-yl) ethylamino]-6-$\alpha,\alpha,\beta,\beta$-tetrafluoroethyl-s-triazine, 2-amino-4-[1-(thianaphthen-3'-yl) ethylaminol-6-trichloromethyl-s-triazine, 2-amino-4-[1-(benzofuran-2'-yl) propylamino]-6-trifluoromethyl-s-triazine, 2-amino-4-[1-(benzofuran-2'-yl) propylamino]-6-$\alpha,\alpha$-dichloroethyl-s-triazine, 2-amino-4-[1-(thianaphthen-2'-yl) propylamino]-6-trifluoromethyl-s-triazine, 2-amino-4-[1-(thianaphthen-2'-yl) propylamino]-6-$\alpha,\alpha$-dichloroethyl-s-triazine, 2-amino-4-[1-(benzofuran-2'-yl) butylamino]-6-trifluoromethyl-s-triazine, 2-amino-4-[1-(thianaphthen-2'-yl) butylamino]-6-trifluoromethyl-s-triazine, 2-amino-4-[1-(5',7'-dichlorobenzofuran-2'-yl) ethlamino]-6-trifluoromethyl-s-triazine, 2-amino-4-[1-(4',7'-dichlorobenzofuran-2'-yl)ethylamino]-6-trifluoromethyl-s-triazine, 2-amino-4-[1-(6'-methylbenzofuran-2'-yl) ethylamino]-6-$\alpha,\alpha$-dichloroethyl-s-triazine, 2-amino-4-[1-(6'-methylbenzofuran-2'-yl) ethylamino]-6-$\alpha,\alpha,\beta,\beta$-tetrafluoroethyl-s-triazine, 2-amino-4-[1-(6'-methylbenzofuran-2'-yl) propylamino]-6-trifluoromethyl-s-triazine, 2-amino-4-[1-(6',7'-dimethylbenzofuran-2'-yl) ethylamino]-6-trifluoromethyl-s-triazine, 2-amino-4-[1-(6',7'-dimethylbenzofuran-2'-yl) ethylamino]-6-$\alpha,\alpha$-dichloroethyl-s-triazine, 2-amino-4-[1-(6',7'-dimethylbenzofuran-2'-yl) ethylamino]-6-$\alpha,\alpha,\beta,\beta$-tetrafluoroethyl-s-triazine, 2-amino-4-[1-(4',7'-dimethylbenzofuran-2'-yl) ethylamino]-6-$\alpha,\alpha$-dichloroethyl-s-triazine, 2-amino-4-[1-4',7'-dimethylbenzofuran-2'-yl) ethylamino]-6-$\alpha,\alpha,\beta,\beta$-tetrafluoromethyl-s-triazine, 2-amino-4-[1-(4',6'-dimethylbenzofuran-2'-yl) ethylamino]-6-trifluoromethyl-s-triazine, 2-amino-4-[1-(4',6'-dimethylbenzofuran-2'-yl) ethylamino]-6-$\alpha,\alpha$-dichloroethyl-s-triazine, 2-amino-4-[1-(4',6'-dimethylbenzofuran-2'-yl) ethylamino]-6-$\alpha,\alpha,\beta,\beta$-tetrafluoromethyl-s-triazine, 2-amino-4-[1-(6'-ethylbenzofuran-2'-yl) ethylamino]-6-trifluoromethyl-s-triazine, 2-amino-4-[1-(6'-isopropylbenzofuran-2'-yl) ethylamino]-6-trifluoromethyl-s-triazine, 2-amino-4-[1-(6'-chlorobenzofuran-2'-yl) ethylamino]-6-trifluoromethyl-s-triazine, 2-amino-4-[1-(6'-fluorobenzofuran-2'-yl) ethylamino]-6-trifluoromethyl-s-triazine, 2-amino-4-[1-(5'-fluorobenzofuran-2'-yl) ethylamino]-6-trifluoromethyl-s-triazine, 2-amino-4-[1-(6'-bromobenzofuran-2'-yl) ethylamino]-6-trifluoromethyl-s-triazine, 2-amino-4-[1-(5'-methoxybenzofuran-2'-yl) ethylamino]-6-trifluoromethyl-s-triazine, 2-amino-4-[1-(6'-ethoxybenzofuran-2'-yl) ethylamino]-6-trifluoromethyl-s-triazine, 2-amino-4-[1-(6'-isopropoxybenzofuran-2'-yl) ethylamino]-6-trifluoromethyl-s-triazine, 2-amino-4-[1-(6'-methylthianaphthen-2'-yl) ethylamino]-6-trifluoromethyl-s-triazine, 2-amino-4-[1-(5'-methylthianaphthen-2'-yl) ethylamino]-6-trifluoromethyl-s-triazine, 2-amino-4-[1-(4',6'-dimethylthianaphthen-2'-yl) ethylamino]-6-trifluoromethyl-s-triazine, 2-amino-4-[1-(4',6'-dimethylthianaphthen-2'-yl) ethylamino]-6-α,α-dichloroethyl-s-triazine, 2-amino-4-[1-(6',7'-dimethylthianaphthen-2'-yl) ethylamino]-6-trifluoromethyl-s-triazine, 2-amino-4-[1-(6',7'-dimethylthianaphthen-2'-yl) ethylamino]-6-α,α-dichloroethyl-s-triazine, 2-amino-4-[1-(6'-chlorothianaphthen-2'-yl) ethylamino]-6-trifluoromethyl-s-triazine, 2-amino-4-[1-(7'-chlorothianaphthen-2'-yl) ethylamino]-6-trifluoromethyl-s-triazine, 2-amino-4-[1-(6'-methoxythianaphthen-2'-yl) ethylamino]-6-trifluoromethyl-s-triazine, 2-amino-4-[1-(4',6'-dimethoxythianaphthen-2'-yl) ethylamino]-6-trifluoromethyl-s-triazine, 2-amino-4-[1-(6',7'-dimethoxythianaphthen-2'-yl) ethylamino]-6-trifluoromethyl-s-triazine, 2-amino-4-[1-(6'-methylthiobenzofuran-2'-yl) ethylamino]-6-trifluoromethyl-s-triazine, 2-amino-4-[1-(6'-methylthiobenzofuran-2'-yl) ethylamino]-6-α,α-dichloroethyl-s-triazine, 2-amino-4-[1-(6'-ethylthiobenzofuran-2'-yl) ethylamino]-6-trifluoromethyl-s-triazine, 2-amino-4-[1-(6'-difluoromethylthiobenzofuran-2'-yl) ethylamino]-6-trifluoromethyl-s-triazine, 2-amino-4-[1-(6'-difluoromethylthiobenzofuran-2'-yl) ethylamino]-6-α,α-dichloroethyl-s-triazine, 2-amino-4-[1-(6'-chloromethylbenzofuran-2'-yl) ethylamino]-6-trifluoromethyl-s-triazine, 2-amino-4-[1-(6'-difluoromethoxybenzofuran-2'-yl) ethylamino]-6-trifluoromethyl-s-triazine, 2-amino-4-[1-(6'-difluoromethoxybenzofurn-2'-yl) ethylamino]-6-α,α-dichloroethyl-s-triazine, 2-amino-4-[1-(6'-chloroethoxybenzofuran-2'-yl) ethylamino]-6-trifluoromethyl-s-triazine, 2-amino-4-[1-(6'-difluoroethylbenzofuran-2'-yl) ethylamino]-6-trifluoromethyl-s-triazine, 2-amino-4-[1-(6'-trifluoromethylbenzofuran-2'-yl) ethylamino]-6-trifluoromethyl-s-triazine, 2-amino-4-[1-(6'-trifluoromethylbenzofuran-2'-yl) ethylamino]-6-α,α-dichloroethyl-s-triazine, 2-amino-4-[1-(2',3'-dihydrobenzofuran-2'-yl) ethylamino]-6-trifluoromethyl-s-triazine, 2-amino-4-[1-(2',3'-dihydrobenzofuran-2'-yl) ethylamino]-6-α,α-dichloroethyl-s-triazine, 2-amino-4-[1-(2',3'-dihydrobenzofuran-2'-yl) propylamino]-6-trifluoromethyl-s-triazine, 2-amino-4-[1-(2',3'-dihydrobenzofuran-3'-yl) ethylamino]-6-trifluoromethyl-s-triazine, 2-amino-4-[1-(2',3'-dihydrothianaphthen-2'-yl) ethylamino]-6-trifluoromethyl-s-triazine, 2-amino-4-[1-(2',3'-dihydrothianaphthen-3'-yl) ethylamino]-6-trifluoromethyl-s-triazine, 2-amino-4-[1-(6'-methyl-2',3'dihydrobenzofuran -2'-yl) ethylamino]-6-trifluoromethyl-s-triazine, 2-amino-4-[1-(4',7'-dimethyl-2',3'-dihydrobenzofuran-2'-yl) ethylamino]-6-trifluoromethyl-s-triazine, 2-amino-4-[1-(6',7'-dimethyl-2',3'-dihydrobenzofuran-2'-yl) ethylamino]-6-trifluoromethyl-s-triazine, 2-amino-4-[1-(4',6'-dimethyl-2',3'-dihydrobenzofuran-2'-yl) ethylamino]-6-trifluoromethyl-s-triazine, 2-amino-4-[1-(6'-methoxy-2',3'-dihydrobenzofuran-2'-yl) ethylamino]-6-trifluoromethyl-s-triazine, 2amino-4-[1-(6'-chloro-2',3'-dihydrobenzofuran-2'yl) ethylamino]-6-trifluoromethyl-s-triazine, 2-amino4-[1-(6'-fluoro-2',3'dihydrobenzofuran-2'-yl) ethylamino]-6-trifluoromethyl-s-triazine, 2-amino-4-[1-(6'-methyl-2',3'-dihydrothianaphthen-2'-yl) ethylamino]-6-trifluoromethyl-s-triazine, 2-amino-4-[1-(4',7'-dimethyl-2',3'-dihydrothianaphthen-2'-yl) ethylamino]-6-trifluoromethyl-s-triazine, 2-amino-4-[1-(4',6'-dimethyl-2',3'-dihydrothianaphthen-2'-yl) ethylamino]-6-trifluoromethyl-s-triazine, 2-amino-4-[1-(4',6'-dimethyl-2'3'-dihydrothianaphthen-2'-yl) ethylamino]-6-α,α-dichloroethyl-s-triazine, 2-amino-4-[1-(6',7'-dimethyl-2',3'-dihydrothianaphthen-2'-yl) ethylamino]-6-trifluoromethyl-s-triazine, 2-amino-4-[1-(6'-isopropyl-2',3'-dihydrothianaphthen-2'-yl) ethylamino]-6-trifluoromethyl-s-triazine, 2-amino-4-[1-(6'-isopropyl-2',3'-dihydrobenzofuran-2'-yl) ethylamino]-6-trifluoromethyl-s-triazine, 2-propionylamino-4-[1-(benzofuran-2'-yl) ethylamino]-6-trifluoromethyl-s-triazine, 2-chloromethylcarbonylamino-4-[1-(benzofuran-2'-yl) ethylamino]-6-trifluoromethyl-s-triazine, 2-bromomethylcarbonylamino-4-[1-(benzofuran-2'-yl) ethylamino]-6-trifluoromethyl-s-triazine, 2-ethoxymethylcarbonylamino-4-[1-(benzofuran-2'-yl) ethylamino]-6-trifluoromethyl-s-triazine, 2-methylthiomethylcarbonylamino-4-[1-(benzofuran-2'-yl) ethylamino]-6-trifluoromethyl-s-triazine, 2-acryloylamino-4-[1-(benzofuran-2'-yl) ethylamino]-6-trifluoromethyl-s-triazine, 2-formylamino-4-[1-(benzofuran-2'-yl) ethylamino]-6-trifluoromethyl-s-triazine, 2-isobutyleneimino-4-[1-(benzofuran-2'-yl) ethylamino]-6-trifluoromethyl-s-triazine, 2-n-butyleneimino-4-[1-(benzofuran-2'-yl) ethylamino]-6-trifluoromethyl-s-triazine, 2-n-propyleneimino-4-[1-(benzofuran-2'-yl) ethylamino]-6-trifluoromethyl-s-triazine, 2-ethoxymethyleneimino-4-[1-(benzofuran-2'-yl) ethylamino]-6-trifluoromethyl-s-triazine, 2-(N,N-dimethyleneimino)-4-[1-(benzofuran-2'-yl) ethylamino]-6-trifluoromethyl-s-triazine, 2-acetylamino-4-[1-(benzofuran-2'-yl) ethylamino]-6-α,α-dichloroethyl-s-triazine, 2-methoxymethylcarbonylamino-4-[1-(benzofuran-2'-yl) ethylamino]-6-α,α-dichloroethyl-s-triazine, 2-chloromethylcarbonylamino-4'[1-(benzofuran-2'-yl) ethylamino]-6-α,α-dichloroethyl-s-triazine, 2-acryloylamino-4-[1-(benzofuran-2'-yl) ethylamino]-6-α,α-dichloroethyl-s-triazine, 2-formylamino-4-[1-(benzofuran-2'-yl) ethylamino]-6-α,α-dichloroethyl-s-triazine, 2-isobutyleneimino-4-[1-(benzofuran-2'-yl) ethylamino]-6-α,α-dichloroethyl-s-triazine, 2-ethyleneimino-4-[1-(benzofuran-2'-yl) ethylamino]-6-α,α-dichloroethyl-s-triazine, 2-acetylamino-4-[1-(thianaphthen-2'-yl) ethylamino]-6-trifluoromethyl-s-triazine, 2-methoxymethylcarbonylamino-4-[1-(thianaphthen-2'-yl) ethylamino]-6-trifluoromethyl-s-triazine, 2-isobutyleneimino-4-[1-(thianaphthen-2'-yl) ethylamino]-6-trifluoromethyl-s-triazine, 2-isobutyleneimino-4-[1-(thianaphthen-3'-yl) ethylamino]-6-trifluoromethyl-s-triazine, 2-methoxymethylcarbonylamino-4-[1-(thianaphthen-3'-yl) ethylamino]-6-trifluoromethyl-s-triazine, 2-acetylamino-4-[1-(4',6'-dimethylbenzofuran-2'-yl) ethylamino]-6-trifluoromethyl-s-triazine, 2-isobutyleneimino-4-[1-(4',6'-dimethylbenzofuran-2'-yl) ethylamino]-6-trifluoromethyl-s-triazine, 2-acetylamino-4-[1-(2'-3'-dihydrobenzofuran-2'-yl) ethylamino]-6-trifluoromethyl-s-triazine, 2-isobutyleneimino-4-[1-(2',3'-dihydrobenzofuran-2'-yl) ethylamino]-6-trifluoromethyl-s-triazine, 2-methoxymethylcarbonylamino-4-[1-(2',3'-dihydrothianaphthen-2'-yl) ethylamino]-6-trifluoromethyl-s-triazine, 2-isobutyleneimino-4-[1-(2',3'-dihydrothianaphthen-2'-yl) ethylamino]-6-trifluoromethyl-s-triazine, 2-methoxymethylcarbonylamino-4-[1-(2',3'-dihydrothianaphthen-3'-yl) ethylamino]-6-trifluoromethyl-s-triazine, 2-isobutyleneimino-4-[1-(2',3'-dihydrothianaphthen-3'-yl) ethylamino]-6-trifluoromethyl-s-triazine, 2-methoxymethylcarbonylamino-4-[1-(2',3'-dihydrobenzofuran-3'-yl) ethylamino]-6-trifluoromethyl-s-triazine, 2-isobutyleneimino-4-[1-(2',3'-dihydrobenzofuran-3'-yl)

ethylamino]-6-trifluoromethyl-s-triazine, 2-acetylamino-4-[1-(6'-methylbenzofuran-2'-yl) ethylamino]-6-trifluoromethyl-s-triazine, 2-isobutyleneimino-4-[1-(6'-methylbenzofuran-2'-yl) ethylamino]-6-trifluoromethyl-s-triazine, 2-acetylamino-4-[1-(4',7'-dimethylbenzofuran-2'-yl) ethylamino]-6-trifluoromethyl-s-triazine, 2-isobutyleneimino-4-[1-(4',7'-dimethylbenzofuran-2'-yl) ethylamino]-6-trifluoromethyl-s-triazine and the like.

The triazine derivatives of the present invention represented by the above given general formula [I] or general formula [II] can be prepared by various methods. The methods for the preparation thereof with high efficiency among them include the above described "method 1" to "method 6" and the methods for the preparation of the triazine derivatives represented by the general formula [I] include the above described method 1, method 3 and method 5 while the methods for the preparation of the triazine derivatives represented by the general formula [II] include the above described method 2, method 4 and method 6.

According to the method 1, a salt of a benzofuranyl alkyl amine represented by the general formula [III] and cyanoguanidine are reacted to give a salt of a benzofuranyl biguanide represented by the general formula [IV], which is then reacted with an alkyl ester represented by the general formula [V] to give the desired triazine derivative represented by the general formula [I-A] (this corresponds to a part of the triazine derivatives of the general formula [I]. Namely, it is a triazine derivative with $NH_2$ as the $R^3$ in the formula [I]).

Salts of a benzofuranyl alkyl amine represented by the general formula [III] include, for example, salts of 1-benzofuran-2-yl ethyl amine, salts of 1-benzofuran-3-yl ethyl amine, salts of 1-thianaphthen-2-yl ethyl amine, salts of 1-thianaphthen-3-yl ethyl amine, salts of 1-benzofuran-2-yl propyl amine, salts of 1-benzofuran-2-yl butyl amine, salts of 1-thianaphthen-2-yl propyl amine, salts of 1-thianaphthen-2-yl butyl amine, salts of 1-(6-chlorobenzofuran-2-yl) ethyl amine, salts of 1-(5-chlorobenzofuran-2-yl) ethyl amine, salts of 1-(4,7-dimethyl benzofuran-2-yl) ethyl amine, salts of 1-(4,6-dimethyl benzofuran-2-yl) ethyl amine, salts of 1-(6-ethyl benzofuran-2-yl) ethyl amine, salts of 1-(6-isopropyl benzofuran-2-yl) ethyl amine, salts of 1-(6-fluoro benzofuran-2-yl) ethyl amine, salts of 1-(5-fluoro benzofuran-2-yl) ethyl amine, salts of 1-(6-bromo benzofuran-2-yl) ethyl amine, salts of 1-(5-bromo benzofuran-2-yl) ethyl amine, salts of 1-(6-methoxy benzofuran-2-yl) ethyl amine, salts of 1-(5-methoxy benzofuran-2-yl) ethyl amine, salts of 1-(5-ethoxy benzofuran-2-yl) ethyl amine, salts of 1-(6-isopropoxy benzofuran-2-yl) ethyl amine, salts of 1-(5,7-dichloro benzofuran-2-yl) ethyl amine, salts of 1-(4,7-dichloro benzofuran-2-yl) ethyl amine, salts of 1-(6-methyl benzofuran-2-yl) ethyl amine, salts of 1-(6-methyl benzofuran-2-yl) propyl amine, salts of 1-(6,7-dimethyl benzofuran-2-yl) ethyl amine, salts of 1-(6-methyl thianaphthen-2-yl) ethyl amine, salts of 1-(5-methyl thianaphthen-2-yl) ethyl amine, salts of 1-(4,6-dimethyl thianaphthen-2-yl) ethyl amine, salts of 1-(6,7-dimethyl thianaphthen-2-yl) ethyl amine, salts of 1-(6-chloro thianaphthen-2-yl) ethyl amine, salts of 1-(7-chloro thianaphthen-2-yl) ethyl amine, salts of 1-(6-methoxy thianaphthen-2-yl) ethyl amine, salts of 1-(4,6-dimethoxy thianaphthen-2-yl) ethyl amine, salts of 1-(6,7-dimethoxy thianaphthen-2-yl) ethyl amine, salts of 1-(6-methylthio benzofuran-2-yl) ethyl amine, salts of 1-(6-ethylthio benzofuran-2-yl) ethyl amine, salts of 1-(6-difluoromethylthio benzofuran-2-yl) ethyl amine, salts of 1-(6-chloromethyl benzofuran-2-yl) ethyl amine, salts of 1-(6-difluoroethyl benzofuran-2-yl) ethyl amine, salts of 1-(6-trifluoromethyl benzofuran-2-yl) ethyl amine, salts of 1-(6-difluoromethoxy benzofuran-2-yl) ethyl amine, salts of 1-(6-chloroethoxy benzofuran-2-yl) ethyl amine and the like. In carrying out the reaction of the salt of benzofuranyl alkyl amine represented by the above given general formula [III] and cyanoguanidine, these two compounds may be used in an about equimolar proportion and, although solvents are not always necessary, there can be used alcohols such as methanol, ethanol, isopropanol and the like, ketones such as acetone, methyl ethyl ketone, cyclohexanone and the like, aliphatic hydrocarbons such as n-hexane, n-heptane and the like, cyclic hydrocarbons such as benzene, decalin, alkyl naphthalenes and the like, chlorinated hydrocarbons such as ethylene dichloride, chlorobenzene, dichlorobenzene and the like and ethers such as tetrahydrofuran, dioxane and the like as well as kerosine and the like. The temperature of reaction is not particularly limitative and it can proceed satisfactorily at a temperature from low to high temperatures or, in particular, in the range from 80° to 200° C.

This reaction gives a salt of a benzofuranyl biguanide derivative represented by the general formula [IV] which, in the method 1 of the present invention, is reacted with an alkyl ester $R^2COOR^6$ of the general formula [V] to prepare the desired triazine derivative represented by the general formula [I-A]. Usually, this reaction proceeds efficiently in a solvent such as alcohols, e.g. methanol, ethanol, isopropanol and the like, various kinds of ketones, aliphatic hydrocarbons, various kinds of ethers, various kinds of cyclic hydrocarbons, chlorinated hydrocarbons and the like in the presence of a catalyst such as a base and the like at around 10° to 100° C.

In the method 3 of the present invention to follow, the amino group-containing triazine derivative represented by the general formula [I-A] and obtained by the above mentioned method 1 is reacted with a carboxylic acid of the above given general formula [VI], carboxylic acid anhydride of the general formula [VII], halide of carboxylic acid of the general formula [VIII] or carboxylic acid ester of the general formula [IX]. When a halide of carboxylic acid of the general formula [VIII] is used, it is usual in this reaction that, though dependent on the type of the compound used, the above mentioned halide of carboxylic acid is used in a proportion of 1 to 3 times by moles relative per mole of the amino group-containing triazine derivative of the general formula [I-A] and it is preferable, although solvents are not always necessary, to use aromatic hydrocarbons such as benzene, toluene, xylene and the like, halogenated hydrocarbons such as chloroform, methylene chloride and the like, ketones such as acetone, methyl ethyl ketone and the like, aliphatic hydrocarbons such as hexane, heptane and the like, ethers such as tetrahydrofuran, ethyl ether and the like or basic solvents such as pyridine and the like, and so on. Further, it is effective to add a base such as triethyl amine and the like to this reaction system. Although the temperature of the reaction is not particularly limitative, it can proceed at a temperature of from low to high temperatures or, in particular, in the range from −20° C. to 80° C.

When a carboxylic acid ester of the general formula [IX] is used, in the next place, it should be used in an amount at least equimolar to the amino group-containing triazine derivative of the general formula [I-A] and, although solvents are not always necessary, it is preferable to use water, aromatic hydrocarbons such as benzene, toluene, xylene and the like, ketones such as acetone, methyl ethyl ketone and the like, aliphatic hydrocarbons such as hexane, heptane and the like, ethers such as tetrahydrofuran, ethyl ether and the like and alcohols such as methanol, ethanol and the like as well as dimethyl formamide and dimethyl sulfoxide as the solvent. Further, it is effective to admix the reaction mixture with a base such as sodium methoxide, sodium ethoxide, n-butyl lithium, sodium hydride and the like. Although the temperature of the reaction is not particularly limitative, furthermore, it can proceed satisfactorily at a temperature of from low to high temperatures or, in particular, in the range from 10° to 100° C.

When a carboxylic acid of the general formula [VI] or carboxylic acid anhydride of the general formula [VII] is used, it can be applied correspondingly as in case of using carboxylic acid ester.

According to the method 3 of the present invention, the desired triazine derivative represented by the general formula [I-B] can be obtained by the above described reaction.

In the method 5 of the present invention, furthermore, the triazine derivative of the general formula [I-A] (amino group-containing triazine derivative) obtained by the above described method 1 is reacted with an aldehyde of the general formula [X] or acetal of the general formula [XI].

In this reaction, the aldehyde of the general formula [X] or acetal of the general formula [XI] should be used in an approximately equimolar amount relative to the amino group-containing triazine derivative of the general formula [I-A] and, although solvents are not always necessary, aromatic hydrocarbons such as benzene, toluene, xylene and the like, halogenated hydrocarbons such as chloroform, methylene chloride and the like, aliphatic hydrocarbons such as hexane, heptane and the like, ethers such as tetrahydrofuran, ethyl ether and the like, and so on can be used as a preferable solvent. Further, it is preferable to use a dehydrating agent such as potassium hydroxide and the like and a catalyst such as p-toluene sulfonic acid and the like in this reaction mixture and, although the temperature of the reaction is not particularly limitative, it can proceed satisfactorily at a temperature of from low to high temperatures or, in particular, in the range from 10° to 100° C.

According to the method 5 of the present invention as above, the desired triazine derivative represented by the general formula [I-C] can be obtained by the above described reaction.

In the next place, the triazine derivative of the present invention represented by the above given general formula [II] (triazine derivative having a dihydrobenzo(thia)furanyl group) can be prepared in the same manner as the triazine derivative of the general formula [I], for which methods having high efficiency include the method 2, method 4 and method 6 of the present invention described before.

According to the method 3, the salt of a dihydrobenzofuranyl alkyl amine represented by the general formula [III'] is reacted with cyanoguanidine to give a salt of a dihydrobenzofuranyl biguanide represented by the general formula [IV'], which is then reacted with an alkyl ester represented by the general formula [V] to give the desired triazine derivative represented by the general formula [II-A] (This corresponds to a part of the triazine derivatives of the general formula [II]. Namely, it is a triazine derivative with $NH_2$ as the $R^3$ in the formula [II].).

Exemplary of the salt of a dihydrobenzofuranyl alkyl amine represented by the general formula [III'] are, for example, salts of 1-(2,3-dihydrobenzofuran-2-yl) ethyl amine, salts of 1-(2,3-dihydrobenzofuran-2-yl) propyl amine, salts of 1-(2,3-dihydrobenzofuran-3-yl) ethyl amine, salts of 1-(2,3-dihydrothianaphthen-3-yl) ethyl amine, salts of 1-(2,3-dihydrothianaphthen-2-yl) ethyl amine, salts of 1-(6-methyl-2,3dihydrobenzofuran-3-yl) ethyl amine, salts of 1-(4,7-dimethyl-2,3-dihydrobenzofuran-2-yl) ethyl amine, salts of 1-(6,7-dimethyl-2,3-dihydrobenzofuran-2-yl) ethyl amine, salts of 1-(4,6-dimethyl-2,3-dihydrobenzofuran-2-yl) ethyl amine, salts of 1-(6-methoxy-2,3-dihydrobenzofuran-2-yl) ethyl amine, salts of 1-(6-chloro-2,3-dihydrobenzofuran-2-yl) ethyl amine, salts of 1-(6-fluoro-2,3-dihydrobenzofuran-2-yl) ethyl amine, salts of 1-(6-methyl-2,3-dihydrothianaphthen-2-yl) ethyl amine, salts of 1-(4,7-dimethyl-2,3-dihydrothianaphthen-2-yl) ethyl amine, salts of 1-(4,6-dimethyl-2,3-dihydrothianaphthen-2-yl) ethyl amine, salts of 1-(6,7-dimethyl-2,3-dihydrothianaphthen-2-yl) ethyl amine, salts of 1-(6-isopropyl-2,3-dihydrothianaphthen-2-yl) ethyl amine, salts of 1-(6-isopropyl-2,3-dihydrobenzofuran-2-yl) ethyl amine and the like.

The reaction of the method 2 of the present invention can be carried out in the same manner as in the above described method 1 excepting replacement of the salt of the dihydrobenzofuranyl alkyl amine represented by the general formula [III'] with the salt of a benzofuranyl alkyl amine represented by the general formula [III].

According to this method 2, the amino group-containing triazine derivative represented by the general formula [II-A] can be obtained in a high purity and in a high yield.

In the method 4 of the present invention, furthermore, the amino group-containing triazine derivative represented by the general formula [II-A] is prepared according to the above described method 2 of the present invention and then this triazine derivative is reacted with a carboxylic acid of the above given general formula [VI], carboxylic acid anhydride of the general formula [VII], halide of a carboxylic acid of the general formula [VIII] or carboxylic acid eater of the general formula [IX] to give the desired triazine derivative represented by the general formula [II-B].

Incidentally, this method 4 is practiced in accordance with the method 3 described above.

In the method 6 of the present invention, then, the amino group-containing triazine derivative represented by the general formula [II-A] is prepared according to the above described method 2 of the present invention followed by the reaction of this triazine derivative with an aldehyde of the general formula [X] or acetal of the general formula [XI] to give the desired triazine derivative represented by the general formula [II-C].

Incidentally, this method 6 can be practiced in accordance with the above described method 5.

As is described above, each of the triazine derivatives of the general formula [I-A] obtained by the method 1 of the present invention, the triazine derivatives of the general formula [I-B] obtained by the method 3 and the triazine derivatives of the general formula [I-C] obtained by the method 5 is included within the triazine derivatives of the present invention represented by the general formula [I] and is a novel compound.

Further, each of the triazine derivatives of the general formula [II-A] obtained by the method 2 of the present invention, the triazine derivatives of the general formula [II-B] obtained by the method 4 and the triazine derivatives of the general formula [II-C] obtained by the method 6 is included within the triazine derivatives of the present invention represented by the general formula [II] and is a novel compound.

Furthermore, the triazine derivatives represented by the general formula [I] or [II] is suitable as a herbicide since they can suppress germination and growth of weeds with high selectivity. Besides, they can exhibit a excellent herbicidal effect not only against annual broadleaf weeds such as Rotala indica (Willd.) Koehne var. uligirosa (Miq.) Koehne., Lindernia pyxidaria L. and Monochoria vaginalis Presl var. plantaginea (Roxb.) Solms-Laub., species of Cyperaceae such as Cyperus difformis L., and Graminceae such as Echinochloa crus-galli L., as well as perennial weeds such as Scirpus juncoides Roxb. var. Hotarui Ohwi, Cyperus serotinus Rottb. and Sagittaria pygmaea Miq. which are now considered to be difficult to control, without causing phytotoxicity to the paddy rice plants.

Furthermore, these triazine derivatives exhibit excellent herbicidal effects against troublesome weeds such as sicklepod (Cassia obtusifolia L.), tallmorning glory (Ipomoea purpures (L) Roth), velvet leaf (Abutilon theophrasti Medik), common chickweed(Stellaria media L.), birdeye speedwell(Veronica persica Poir), badysthumb(polygonum persicaria L.), field biolet(viola arvensis MURR.) and wild mustard(Sinapis arvensis L.) without injuring corns and grain sorghums which are important upland crops.

In the next place, the herbicide of the present invention comprises the compounds of the above described invention or, namely, the triazine derivatives represented by the general formula [I] or [II] as an active ingredient and can be applied as formulated in the forms of wettable powders, emulsifiable concentrate, dusts, granules and the like prepared by mixing these compounds with a liquid carrier such as organic solvents and the like or a solid carrier such as mineral fine powders and the like. A surface active agent may be added thereto in the formulation in order to give emulsifiability, dispersibility, spreadability and the like.

When the herbicide of the present invention is used in the form of wettable powder, a suitable form of the preparation is usually a composition compounded from 10 to 55% by weight of the above described triazine derivative of the invention as the active ingredient, from 40 to 88% by weight of a solid carrier and from 2 to 5% by weight of a surface active agent. When it is used in the form of emulsifiable concentrate, the preparation is usually formulated from 20 to 50% by weight of the triazine derivative of the present invention as the active ingredient, from 35 to 75% by weight of a solvent and from 5 to 15% by weight of a surface active agent.

When it is used in the form of dust, on the other hand, the preparation should usually be formulated from 1 to 15% by weight of the triazine derivative of the present invention as the active ingredient, from 80 to 97% by weight of a solid carrier and from 2 to 5% by weight of a surface active agent. Further, when it is used in the form of a granule, the preparation should be formulated from 0.1 to 15% by weight of the triazine derivative of the present invention as the active ingredient, from 80 to 97.9% by weight of a solid carrier and from 2 to 5% by weight of a surface active agent. The solid carrier here used should be a finely divided mineral powder which is exemplified by oxides such as diatomaceous earth, slaked lime and the like, phosphates such as apatite and the like, sulfates such as gypsum and the like, silicates such as talc, pyrophillite, clay, kaolin, bentonite, acid clay, white carbon, quartz powder, powder of silica stone and the like, and so on.

And, organic solvents are used as the solvent and exemplary thereof are aromatic hydrocarbons such as xylene, toluene, benzene and the like, chlorinated hydrocarbons such as o-chlorotoluene, trichloromethane, trichloroethylene and the like, alcohols such as cyclohexanol, amyl alcohol, ethylene glycol and the like, ketones such as isophorone, cyclohexanone, cyclohexenyl cyclohexanone and the like, ethers such as butyl cellosolve, dimethyl ether, methyl ethyl ether and the like, esters such as isopropyl acetate, benzyl acetate, methyl phthalate and the like and amides such as dimethyl formamide and the like as well as mixtures thereof.

Further, as the surface active agent can be used any of anionic, nonionic, cationic and amphoteric (amide acids, betaine and the like) ones.

The triazine derivatives as novel compounds represented by the general formula [I] or [II] of the present invention can exhibit high herbicidal effects not only against annual weeds as a matter of course but also against perennial weeds so that they are very useful as a highly selective herbicide not casing any injury against paddy rice plants. Besides, when they are used as a foliage-applied herbicide for upland crops such as corns, wheats, barleys, oats, grain sorghums and the like, excellent effects can be exhibited as compared to commercially available foliage-applied herbicide for upland crops.

Incidentally, the herbicide of the present invention may comprise, in combination with the triazine derivative represented by the general formula [I] or [II] as the active ingredient, other herbicidal constituents. Such other herbicidal constituents include those hitherto marketed herbicides exemplified by phenoxy-based herbicides, diphenyl ether-based herbicides, triazine-based herbicides, urea-based herbicides, carbamate-based herbicides, thiol carbamate-based herbicides, acid anilide-based herbicides, pyrazole-based herbicides, phosphate-based herbicides, sulfonyl urea-based herbicides, oxadiazones and the like. Optionally, the herbicide of the present invention can be compounded according to need with insecticides, fungicides, plant regulators, fertilizers and the like in combination.

REFERENCE EXAMPLE 1.

A mixture of 9.9 g (50 m moles) of 1-(benzofuran-2-yl) ethyl amine hydrochloride and 4.2 g (50 m moles) of cyanoguanidine in 35 ml of o-dichlorobenzene was heated under agitation at 140° to 150° C. for 8 hours.

After completion of the reaction and cooling, the precipitates were collected by filtration and washed three times with 5 ml of toluene. Thereafter, the solvent was distilled away under reduced pressure to give 13.8 g of solid 1-benzofuran-2'-yl) eithyl biguanide hydrochloride (yield 94%). The melting point thereof was 211.1° to 212.4° C. Following is the structural formula of this product.

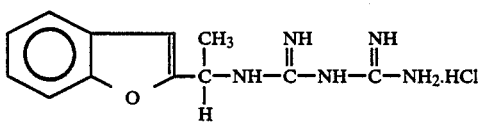

REFERENCE EXAMPLES 2 TO 6

The same procedure as in Example 1 was undertaken except that 1-(benzofuran-2-yl) ethyl amine hydrochloride in Reference Example 1 was replaced with an ethyl amine hydrochloride indicated in Table 1 to give the respective ethyl biguanide hydrochloride. The structural formula and yields of the thus obtained ethyl biguanide hydrochlorides are shown in Table 1.

lowed by recrystallization from hexane-ethyl ether to give 2.82 g of white 2-amino-4-[1-(benzofuran-2'-yl) ethyl amino]-6-trifluoromethyl-s-triazine (compound I). Tables 2 to 4 show the obtained amount, yield, results of analysis, structural formula and so on of this material.

PREPARATION EXAMPLES 2 TO 6

Compounds 2 to 6 were obtained by undertaking the same procedure as in Preparation Example 1 except that the trifluoroacetic acid ethyl ester as the reactant II was replaced with each 20 m moles of the esters indicated in Table 2. Tables 2 to 4 show the obtained amounts, yields, results of analysis, structural formulas and so on of these compounds.

PREPARATION EXAMPLES 7 TO 11

TABLE 1

| | Ethyl amine hydrochloride used | Structural formula of ethyl biguanide hydrochloride obtained | Yield (%) |
|---|---|---|---|
| Reference Example 2 | 1-(5-Chlorobenzofuran-2-yl) ethyl amine hydrochloride | | 96 |
| Reference Example 3 | 1-(6-Methylbenzofuran-2-yl) ethyl amine hydrochloride | | 95 |
| Reference Example 4 | 1-(5-Methoxybenzofuran-2-yl) ethyl amine hydrochloride | | 93 |
| Reference Example 5 | 1-(4,7-Dimethylbenzofuran-2-yl) ethyl amine hydrochloride | | 94 |
| Reference Example 6 | 1-(Thianaphthen-3-yl) ethyl amine hydrochloride | | 89 |

PREPARATION EXAMPLE 1

Into 20 ml of dehydrated methyl alcohol was added 0.46 g of sodium bit by bit to form sodium methoxide and then 2.92 g (10 m moles) of 1-(benzofuran-2'-yl) ethyl biguanide hydrochloride obtained in Reference Example 1 were added thereto as the reactant I to be agitated for 30 minutes at room temperature. Thereafter, 2.38 ml (20 m moles) of trifluoroacetic acid ethyl ester as the reactant II were added thereto dropwise and agitated for 10 hours at room temperature. After completion of the reaction, the mixture was poured into 100 ml of water and extracted three times with 50 ml of ethyl acetate. The ethyl acetate layer was dried over anhydrous sodium sulfate followed by removal of ethyl acetate by distillation under reduced pressure. The residue was purified by silica gel column chromatography (developer solvent: hexane: ethyl acetate=4:1) fol- Compounds 7 to 11 were obtained by undertaking the same procedure as in Preparation Example 1 except that the 1-(benzofuran-2-yl) ethyl biguanide hydrochloride as the reactant I was replaced with the biguanide hydrochlorides indicated in Table 2. Tables 2 to 4 show the obtained amounts, yields, results of analysis, structural formulas and so on of these compounds.

PREPARATION EXAMPLES 12 AND 13

Compounds 12 and 13 were obtained by undertaking the same procedure as in Preparation Example 1 except that 1-(benzofuran-2-yl) ethyl biguanide hydrochloride was used as the reactant I and trifluoroacetic acid ethyl ester was used as the reactant II. Tables 2 to 4 show the obtained amounts, yields, results of analysis, structural formulas and so on of these compounds.

PREPARATION EXAMPLE 14

Into 20 ml of benzene were dissolved 3.23 g (10 m moles) of 2-amino-4-[1-(benzofuran-2′-yl) ethyl amino]-6-trifluoromethyl-s-triazine (compound I) obtained in Preparation Example 1 as the reactant 1 and then 1.57 g (20 m moles) of triethyl amine were added thereto. Thereafter, 2.02 g (20 m moles) of acetyl chloride as the reactant II were added dropwise thereto under cooling with ice and agitation followed by heating under reflux for 3 hours at room temperature. After cooling, the benzene layer was washed with water and dried over anhydrous sodium sulfate followed by removal of benzene by distillation under reduced pressure. The residue was purified by developing in silica gel column chromatography (developer solvent: toluene: ethyl acetate=8:2) and recrystallized from acetone-water to give 1.31 g of white crystals of 2-acetylamino-4-[1-(benzofuran-2′-yl) ethyl amino]-6-trifluoromethyl-s-triazine (compound 14). Tables 2 to 4 show the obtained amount, yield, results of analysis, structural formula and so on of this material.

PREPARATION EXAMPLE 15

A mixture of 3.23 g (10 m moles) of 2-amino-4-[1-(benzofuran-2′-yl) ethyl amino]-6-trifluoromethyl-s-triazine (compound 1) obtained in Preparation Example 1 as the reactant I with admixture of 1.93 g (10 m moles) of a 28% methanol solution of sodium methoxide and 10 ml of methanol was heated at 50° C. and then freed from methanol by distillation under reduced pressure. The residue was admixed with 20 ml of ethyl cyclopropane carboxylate as the reactant II and heated at 50° C. followed by addition of 20 ml of water. The layer of ethyl cyclopropane carboxylate was washed with water followed by removal of the ethyl cyclopropane carboxylate by distillation under reduced pressure. The residue was purified by developing in silica gel column chromatography (developer solvent: toluene:ethyl acetate=8:2) to give 1.84 g of colorless and resinous 2-cyclopropyl carbonyl amino-4-[1-(benzofuran-2′-yl) ethyl amino]-6-trifluoromethyl-s-triazine (compound 15). Tables 2 to 4 show the obtained amount, yield, results of analysis, structural formula and so on of this material.

PREPARATION EXAMPLE 16

The same procedure as in Preparation Example 15 was undertaken except that the ethyl cyclopropane carboxylate as the reactant II was replaced with ethyl methoxyacetate and 2.53 g of colorless and resinous 2-methoxycarbonylamino-4-[1-(benzofuran-2′-yl) ethyl amino]-6-trifluoromethyl-s-triazine (compound 16). Tables 2 to 4 show the obtained amount, yield, results of analysis, structural formula and so on of this material.

PREPARATION EXAMPLE 17

Into 20 ml of dehydrated methyl alcohol was added 0.46 g of sodium bit by bit to form sodium methoxide and then 2.92 g (10 m moles) of 1-(benzofuran-2′-yl) ethyl biguanide hydrochloride obtained in Reference Example 1 were added thereto as the reactant I to be agitated for 30 minutes at room temperature. Thereafter, 2.86 g (20 m moles) of dichloroacetic acid methyl ester as the reactant II were added thereto dropwise and agitated for 10 hours at room temperature. After completion of the reaction, the mixture was poured into 100 ml of water and extracted three times with 50 ml of ethyl acetate. The ethyl acetate layer was dried over anhydrous sodium sulfate followed by removal of ethyl acetate by distillation under reduced pressure. The residue was purified by silica gel column chromatography (developer solvent: hexane:ethyl acetate=4:1) followed by recrystallization from ethanol-water to give 2.96 g of white 2-amino-4-[1-(benzofuran-2′-yl) ethyl amino]-6-dichloromethyl-s-triazine (compound 17). Tables 2 to 4 show the obtained amount, yield, results of analysis, structural formula and so on of this material.

PREPARATION EXAMPLES 18 TO 21

Compounds 18 to 21 were obtained by undertaking the same procedure as in Preparation Example 17 except that the dichloroacetic acid methyl ester as the reactant II was replaced with each 20 m moles of the esters indicated in Table 2. Tables 2 to 4 show the obtained amounts, yields, results of analysis, structural formulas and so on of these compounds.

TABLE 2

| Preparation Example No. (Compound No.) | Reactants I | Reactants II | Amount obtained (g) | Yield (%) | Melting point (°C.) | Elementary analysis* (%) C | H | N | Cl |
|---|---|---|---|---|---|---|---|---|---|
| 1 (1) | Reference Example 1 | Ethyl ester of trifluoroacetic acid | 2.82 | 87 | 159.4–160.1 | 51.5 (52.0) | 3.4 (3.7) | 21.7 (21.7) | — |
| 2 (2) | Reference Example 1 | Methyl ester of α, α, β, β-tetrafluoropropionic acid | 2.14 | 60 | 158.2–158.6 | 51.3 (50.7) | 3.4 (3.7) | 19.2 (19.7) | — |
| 3 (3) | Reference Example 1 | Ethyl ester of chlorodifluoroacetic acid | 2.04 | 60 | 172.8–173.9 | 50.5 (49.5) | 3.6 (3.6) | 20.2 (20.6) | 10.3 (10.4) |
| 4 (4) | Reference Example 1 | Methyl ester of α, α-dichloropropionic acid | 2.42 | 69 | 154.4–154.9 | 51.0 (51.1) | 4.2 (4.3) | 19.7 (19.9) | 19.9 (20.1) |
| 5 (5) | Reference Example 1 | Ethyl ester of monofluoroacetic acid | 2.44 | 80 | 138.8–141.5 | 55.5 (55.1) | 4.2 (4.3) | 22.6 (22.9) | — |
| 6 (6) | Reference Example 1 | Ethyl ester of difluoroacetic acid | 1.78 | 62 | 162.5–163.5 | 58.1 (58.5) | 4.8 (4.9) | 24.7 (24.4) | — |
| 7 (7) | Reference Example 2 | Ethyl ester of trifluoroacetic acid | 2.61 | 73 | 149.4–150.7 | 46.6 (47.0) | 3.3 (3.1) | 19.8 (19.6) | 10.2 (9.9) |
| 8 (8) | Reference Example 3 | Ethyl ester of trifluoroacetic acid | 2.99 | 80 | 126.9–128.0 | 53.8 (53.4) | 4.1 (4.2) | 20.5 (20.8) | — |
| 9 (9) | Reference Example 4 | Ethyle ester of trifluoroacetic acid | 2.65 | 75 | 144.8–146.1 | 51.4 (51.0) | 4.2 (4.0) | 19.7 (20.0) | — |
| 10 (10) | Reference Example 5 | Ethyl ester of trifluoroacetic acid | 2.74 | 78 | 145.5–146.6 | 55.0 (54.7) | 4.3 (4.6) | 19.8 (20.0) | — |
| 11 (11) | Reference Example 6 | Ethyl ester of trifluoroacetic acid | 2.48 | 73 | 138.0–138.9 | 49.9 (49.6) | 3.4 (3.6) | 20.4 (20.6) | — |

TABLE 2-continued

| Preparation Example No. (Compound No.) | Reactants I | Reactants II | Amount obtained (g) | Yield (%) | Melting point (°C.) | Elementary analysis* (%) C | H | N | Cl |
|---|---|---|---|---|---|---|---|---|---|
| 12 (12) | Reference Example 3 | Ethyl ester of monofluoro-acetic acid | 2.17 | 72 | 189.9–189.4 | 60.0 (59.8) | 5.3 (5.4) | 23.1 (23.2) | — |
| 13 (13) | Reference Example 5 | Ethyl ester of monofluoro-acetic acid | 2.21 | 70 | 182.6–183.6 | 60.5 (60.9) | 5.9 (5.8) | 22.5 (22.2) | — |
| 14 (14) | Preparation Example 1 | Acetyl chloride | 1.31 | 36 | 150.1–151.8 | 52.9 (52.6) | 3.8 (3.9) | 19.0 (19.2) | — |
| 15 (15) | Preparation Example 1 | Ethyl cyclopropane carboxylate | 1.84 | 47 | colorless, resinoid form | 55.0 (55.2) | 4.3 (4.1) | 17.7 (17.9) | — |
| 16 (16) | Preparation Example 1 | Ethyl methoxy acetate | 2.53 | 64 | colorless, resinoid form | 51.8 (51.6) | 4.0 (4.1) | 17.5 (17.7) | — |
| 17 (17) | Reference Example 1 | Ethyl ester of dichloro-acetic acid | 2.96 | 88 | 165.2–166.3 | 50.0 (49.7) | 3.6 (3.9) | 20.5 (20.7) | 21.3 (21.0) |
| 18 (18) | Reference Example 1 | Ethyl ester of trichloro-acetic acid | 1.12 | 30 | colorless, resinoid form | 45.4 (45.1) | 3.0 (3.2) | 18.5 (18.8) | 28.3 (28.5) |
| 19 (19) | Reference Example 1 | Ethyl ester of chloro-acetic acid | 2.73 | 90 | 145.3–147.4 | 55.1 (55.4) | 4.7 (4.6) | 23.4 (23.1) | 11.5 (11.7) |
| 20 (20) | Reference Example 1 | Ethyl ester of penta-fluoropropionic acid | 2.43 | 65 | 172.9–174.4 | 48.1 (48.3) | 3.3 (3.2) | 18.5 (18.8) | — |
| 21 (21) | Reference Example 1 | Ethyl ester of α-chloro butylic acid | 2.49 | 75 | 129.4–131.6 | 57.6 (57.9) | 5.6 (5.5) | 21.4 (21.1) | 10.4 (10.7) |

*The value in brackets shows the theoretical value.

TABLE 3

| Preparation Example No. | Structural formula of triazine derivative | Molecular weight of triazine derivative | Triazine derivative |
|---|---|---|---|
| 1 | [Structure: benzofuran-CH(CH3)-NH-triazine with CF3 and NH2] | $C_{14}H_{12}N_5OF_3$ 323.3 | 2-Amino-4-[1-(benzofuran-2'-yl)ethylamino]-6-trifluoromethyl-s-triazine |
| 2 | [Structure: benzofuran-CH(CH3)-NH-triazine with CF2CF2H and NH2] | $C_{14}H_{13}N_5OF_4$ 355.3 | 2-Amino-4-[1-benzofuran-2'-yl)ethylamino]-6-α,α,β,β-tetrafluoroethyl-s-triazine |
| 3 | [Structure: benzofuran-CH(CH3)-NH-triazine with CF2Cl and NH2] | $C_{14}H_{12}N_5OF_2Cl$ 339.7 | 2-Amino-4-[1-(benzofuran-2'-yl)ethylamino]-6-chloro-difluoromethyl-s-triazine |
| 4 | [Structure: benzofuran-CH(CH3)-NH-triazine with CCl2CH3 and NH2] | $C_{15}H_{15}N_5OCl_2$ 352.3 | 2-Amino-4-[1-(benzofuran-2'-yl)ethylamino]-6-α,α-dichloroethyl-s-triazine |
| 5 | [Structure: benzofuran-CH(CH3)-NH-triazine with CF2H and NH2] | $C_{14}H_{13}N_5OF_2$ 305.3 | 2-Amino-4-[1-(benzofuran-2'-yl)ethylamino]-6-difluoromethyl-s-triazine |

TABLE 3-continued

| Preparation Example No. | Structural formula of triazine derivative | Molecular weight of triazine derivative | Triazine derivative |
|---|---|---|---|
| 6 | 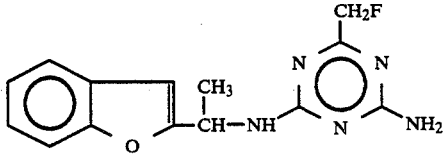 | $C_{14}H_{14}N_5OF$ 287.3 | 2-Amino-4-[1-(benzofuran-2'-yl)ethylamino]-6-monofluoromethyl-s-triazine |
| 7 | 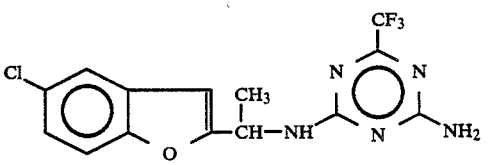 | $C_{14}H_{11}N_5OClF_3$ 357.7 | 2-Amino-4-[1-(5'-chlorobenzofuran-2'-yl)ethylamino]-6-trifluoromethyl-s-triazine |
| 8 | 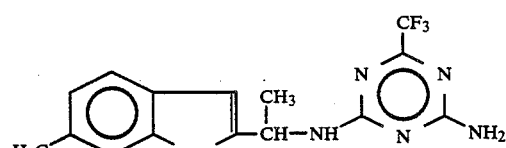 | $C_{15}H_{14}N_5OF_3$ 337.3 | 2-Amino-4-[1-(6'-methylbenzofuran-2'-yl)ethylamino]-6-trifluoromethyl-s-triazine |
| 9 | 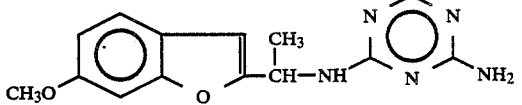 | $C_{15}H_{14}N_5O_2F_3$ 353.3 | 2-Amino-4-[1-(6'-methoxybenzofuran-2'-yl)ethylamino]-6-trifluoromethyl-s-triazine |
| 10 | 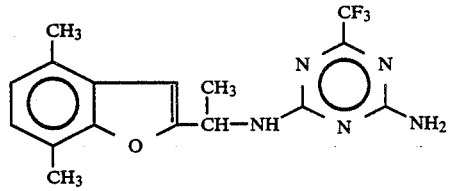 | $C_{16}H_{16}N_5OF_3$ 351.3 | 2-Amino-4-[1-(4',7'-dimethylbenzofuran-2'-yl)ethylamino]-6-trifluoromethyl-s-triazine |
| 11 | 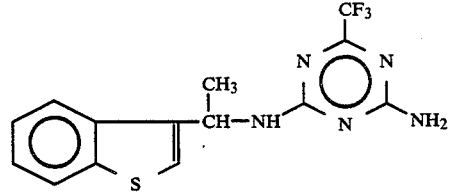 | $C_{14}H_{12}N_5SF_3$ 339.3 | 2-Amino-4-[1-(thianaphthen-3'-yl)ethylamino]-6-trifluoromethyl-s-triazine |
| 12 | 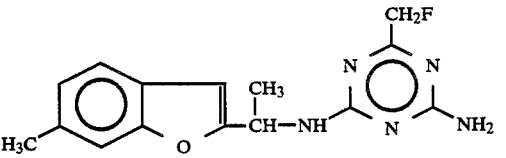 | $C_{15}H_{16}N_5OF$ 301.3 | 2-Amino-4-[1-(6'-methylbenzofuran-2'-yl)ethylamino]-6-monofluoromethyl-s-triazine |
| 13 | 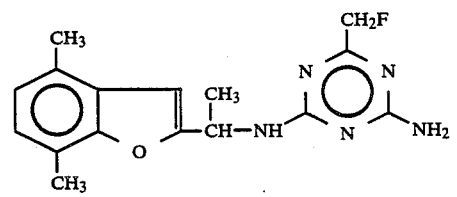 | $C_{16}H_{18}N_5OF$ 315.4 | 2-Amino-4-[1-(4',7'-dimethylbenzofuran-2'-yl)ethylamino]-6-monofluoromethyl-s-triazine |
| 14 | 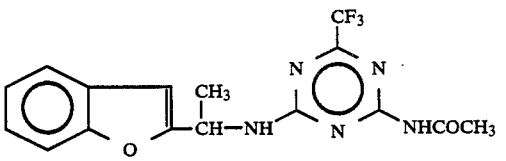 | $C_{16}H_{14}N_5O_2F_3$ 365.3 | 2-Acetylamino-4-[1-(benzofuran-2'-yl)ethylamino]-6-trifluoromethyl-s-triazine |

TABLE 3-continued

| Preparation Example No. | Structural formula of triazine derivative | Molecular weight of triazine derivative | Triazine derivative |
|---|---|---|---|
| 15 | (benzofuran)-CH(CH₃)-NH-[triazine with CF₃]-NHCO-cyclopropyl | $C_{18}H_{16}N_5O_2F_3$ 391.4 | 2-Cyclopropylcarbonylamino-4-[1-(benzofuran-2'-yl)ethylamino]-6-trifluoromethyl-s-triazine |
| 16 | (benzofuran)-CH(CH₃)-NH-[triazine with CF₃]-NHCOCH₂OCH₃ | $C_{17}H_{16}N_5O_3F_3$ 395.3 | 2-Methoxymethylcarbonylamino-4-[1-(benzofuran-2'-yl)ethylamino]-6-trifluoromethyl-s-triazine |
| 17 | (benzofuran)-CH(CH₃)-NH-[triazine with CHCl₂]-NH₂ | $C_{14}H_{13}N_5OCl_2$ 338.2 | 2-amino-4-[1-(benzofuran-2'-yl)ethylamino]-6-dichloromethyl-s-triazine |
| 18 | (benzofuran)-CH(CH₃)-NH-[triazine with CCl₃]-NH₂ | $C_{14}H_{12}N_5OCl_3$ 372.6 | 2-amino-4-[1-(benzofuran-2'-yl)-ethylamino]-6-trichloromethyl-s-triazine |
| 19 | (benzofuran)-CH(CH₃)-NH-[triazine with CH₂Cl]-NH₂ | $C_{14}H_{14}N_5OCl$ 303.8 | 2-amino-4-[1-(benzofuran-2'-yl)-ethylamino]-6-chloromethyl-s-triazine |
| 20 | (benzofuran)-CH(CH₃)-NH-[triazine with C₂F₅]-NH₂ | $C_{15}H_{12}N_5OF_5$ 373.3 | 2-amino-4-[1-(benzofuran-2'-yl)-ethylamino]-6-pentafluoroethyl-s-triazine |
| 21 | (benzofuran)-CH(CH₃)-NH-[triazine with CHClC₂H₅]-NH₂ | $C_{16}H_{18}N_5OCl$ 331.8 | 2-amino-4-[1-(benzofuran-2'-yl)-ethylamino]-6-(α-chloropropyl)-s-triazine |

TABLE 4

| Preparation Example No. | Compound prepared | Infrared spectrum*1 (cm⁻¹) NH₂ | NH | s-triazine | C=O | Proton NMR spectrum*2 (ppm) |
|---|---|---|---|---|---|---|
| 1 | Compound 1 | 3490 3340 | 3280 | 1580 | — | 1.63 (3H, d, CH—C$\underline{H}_3$), 5.36–5.62 (1H, m, C$\underline{H}$—CH₃), 6.57 (1H, s, C=C$\underline{H}$), 7.12–7.53 (4H, m, benzene ring) |
| 2 | Compound 2 | 3480 3340 | 3280 | 1580 | — | 1.62 (3H, d, CH—C$\underline{H}_3$), 5.33–5.50 (1H, m, C$\underline{H}$—CH₃), 6.32 (1H, t, CF₂—CF₂$\underline{H}$), 6.58 (1H, s, C=C$\underline{H}$), 7.12–7.55 (4H, m, benzene ring) |
| 3 | Compound 3 | 3480 3340 | 3320 | 1580 | — | 1.62 (3H, d, CH—C$\underline{H}_3$), 5.38–5.53 (1H, m, C$\underline{H}$—CH₃), 6.59 (1H, s, C=C$\underline{H}$), 7.12–7.58 (4H, m, benzene ring) |
| 4 | Compound 4 | 3500 3410 | 3340 | 1560 | — | 1.63 (3H, d, CH—C$\underline{H}_3$), 2.42 (3H, s, CCl₂—C$\underline{H}_3$), 5.38–5.57 (1H, m, C$\underline{H}$—CH₃), 6.59 (1H, s, C=C$\underline{H}$), 7.13–7.52 (4H, m, benzene ring) |
| 5 | Compound 5 | 3540 3460 | 3360 | 1580 | — | 1.56 (3H, d, CH—C$\underline{H}_3$), 5.40–5.60 (1H, m, C$\underline{H}$—CH₃), 6.04–6.39 (1H, m, —C$\underline{H}$F₂), 6.66 (1H, s, C=C$\underline{H}$), 7.14–7.56 (4H, m, benzene ring) |
| 6 | Compound 6 | 3530 3470 | 3360 | 1570 | — | 1.61 (3H, d, CH—C$\underline{H}_3$), 4.91–5.50 (2H, q, —C$\underline{H}_2$F), 5.39–5.62 (1H, m, C$\underline{H}$—CH₃), 6.65 (1H, s, C=C$\underline{H}$), 7.14–7.56 (4H, m, benzene ring) |
| 7 | Compound 7 | 3540 3500 | 3340 | 1580 | — | 1.66 (3H, d, CH—C$\underline{H}_3$), 5.41–5.60 (1H, m, C$\underline{H}$—CH₃), 6.69 (1H, s, C=C$\underline{H}$), 7.21–7.58 (3H, m, benzene ring + N$\underline{H}$) |

TABLE 4-continued

| Preparation Example No. | Compound prepared | Infrared spectrum*[1] (cm$^{-1}$) | | | | Proton NMR spectrum*[2] (ppm) |
|---|---|---|---|---|---|---|
| | | NH$_2$ | NH | s-triazine | C=O | |
| 8 | Compound 8 | 3540 3460 | 3360 | 1560 | — | 1.58 (3H, d, CH—C$\underline{H}_3$), 2.40 (3H, s, φ-C$\underline{H}_3$), 5.20–5.60 (1H, m, C$\underline{H}$—CH$_3$), 6.48 (1H, s, C=C$\underline{H}$), 6.83–7.48 (4H, m, benzene ring + N$\underline{H}$) |
| 9 | Compound 9 | 3500 3440 | broad absorption band | 1580 | — | 1.63 (3H, d, CH—C$\underline{H}_3$), 3.81 (3H, s, OC$\underline{H}_3$), 5.38–5.56 (1H, m, C$\underline{H}$—CH$_3$), 6.60 (1H, s, C=C$\underline{H}$), 6.80–7.42 (4H, m, benzene ring + N$\underline{H}$) |
| 10 | Compound 10 | 3540 3480 | 3350 | 1580 | — | 1.65 (3H, d, CH—C$\underline{H}_3$), 2.38 (6H, s, φ-C$\underline{H}_3$ × 2), 5.41–5.56 (1H, m, C$\underline{H}$—CH$_3$), 7.71 (1H, s, Cad,4 C$\underline{H}$), 6.80–6.95 (4H, m, benzene ring + NH$_2$) |
| 11 | Compound 11 | 3540 1500 | 3360 | 1570 | — | 1.69 (3H, d, CH-CH$_3$), 5.64–5.80 (1H, m, C$\underline{H}$—CH$_3$), 7.31–7.97 (5H, m, benzene ring + C=C$\underline{H}$) |
| 12 | Compound 12 | 3510 3450 | 3350 | 1560 | — | 1.56 (3H, d, CH—C$\underline{H}_3$), 2.38 (3H, s, φ-C$\underline{H}_3$), 4.91–5.04 (2H, q, C$\underline{H}_2$F), 5.36–5.56 (1H, m, C$\underline{H}$—CH$_3$), 6.68 (1H, s, C=C$\underline{H}$), 6.96–7.40 (4H, m, benzene ring + NH) |
| 13 | Compound 13 | broad absorption band | 3360 | 1550 | — | 1.56 (3H, d, CH—C$\underline{H}_3$), 2.36 (6H, s, φ-C$\underline{H}_3$ × 2), 4.94–5.06 (2H, d, —C$\underline{H}_2$F), 5.37–5.56 (1H, m, C$\underline{H}$—CH$_3$), 6.66 (1H, s, C=C$\underline{H}$), 6.84–6.93 (2H, m, benzene ring) |
| 14 | Compound 14 | — | 3280 | 1560 | 1690 | 1.71 (3H, d, CH—C$\underline{H}_3$), 2.62 (3H, s, COC$\underline{H}_3$), 5.49–5.66 (1H, m, C$\underline{H}$—CH$_3$), 6.64 (1H, s, C=C$\underline{H}$), 7.14–7.56 (4H, m, benzene ring) |
| 15 | Compound 15 | — | 3280 | 1560 | 1690 | 0.90–1.21 (4H, m, Cyclopropyl group (CH$_2$)$_2$), 1.71 (3H, d, CH—C$\underline{H}_3$), 2.88–3.03 (1H, m, Cyclopropyl group C$\underline{H}$), 5.45–5.61 (1H, m, C$\underline{H}$—CH$_3$), 6.60 (1H, s, C=CH), 7.13–7.56 (4H, m, benzene ring) |
| 16 | Compound 16 | — | broad absorption band | 1550 | 1710 | 1.60 (3H, d, CH—C$\underline{H}_3$), 3.38 (3H, s, OC$\underline{H}_3$), 4.03 (2H, s, COC$\underline{H}_2$—), 5.40–5.56 (1H, m, C$\underline{H}$—CH$_3$), 6.54 (1H, s, C=C$\underline{H}$), 7.06–7.46 (4H, m, benzene ring) |
| 17 | Compound 17 | 3460 | 3320 | 1590 | | 1.61 (3H, d, CH—C$\underline{H}_3$), 5.21–5.73 (1H, m, C$\underline{H}$—CH$_3$) 6.50 (1H, s, C$\underline{H}$\<Cl/Cl), 6.58 (1H, s, —C=C$\underline{H}$) 6.90–7.63 (5H, m, benzene ring + N$\underline{H}$) |
| 18 | Compound 18 | 3520 3430 | 3350 | 1570 | | 1.66 (3H, d, CH—C$\underline{H}_3$), 5.20–5.78 (1H, m, C$\underline{H}$—CH$_3$) 6.66 (1H, s, C=C$\underline{H}$) 7.01–7.73 (5H, m, benzene ring + N$\underline{H}$) |
| 19 | Compound 19 | 3510 3440 | 3350 | 1570 | | 1.62 (3H, d, CH—C$\underline{H}_3$), 4.29 (2H, s, C$\underline{H}_2$—Cl) 5.15–5.79 (1H, m, C$\underline{H}$—CH$_3$) 6.60 (1H, s, C=C$\underline{H}$) 7.00–7.59 (5H, m, benzene ring + N$\underline{H}$) |
| 20 | Compound 20 | 3540 3490 | 3350 | 1580 | | 1.68 (3H, d, CH—C$\underline{H}_3$), 5.26–5.76 (1H, m, C$\underline{H}$—CH$_3$) 6.66 (1H, s, C=C$\underline{H}$—) 7.05–7.58 (5H, m, benzene ring + N$\underline{H}$) |
| 21 | Compound 21 | 3490 | 3340 | 1550 | | 0.94 (3H, t, CH$_2$C$\underline{H}_3$), 1.64 (3H, d, CH—C$\underline{H}_3$) 1.87–2.33 (2H, m, C$\underline{H}_2$—CH$_3$), 4.41 (1H, t, C$\underline{H}$Cl—C$_2$H$_5$) 5.28–5.73 (1H, m, C$\underline{H}$—CH$_3$), 6.67 (1H, s, C=C$\underline{H}$) 7.04–7.63 (4H, m, benzene ring) |

*[1]KBr tablet method
*[2]Solvent: CDCl$_3$ in Preparation Examples 1–4 and 14–16, acetone-d$_6$ in Preparation Examples 5–13. Internal standard: tetramethyl silane

EXAMPLES 1 TO 21

(1) PREPARATION OF HERBICIDES

A carrier for wettable powder was prepared by homogeneously grinding and mixing 97 parts by weight of talc (tradename: Zieklite) as a carrier, 1.5 parts by weight of a salt of alkyl aryl sulfonic acid (tradename: Neopelex, manufactured by Kao Atlas Co.) as a surface active agent and 1.5 parts by weight of a nonionic and anionic surface active agents (tradename: Solpol 800A, manufactured by Toho Kagaku Kogyo Co.).

A herbicide was obtained by uniformly grinding and mixing 90 parts by weight of this carrier for wettable powder and 10 parts by weight of one of the triazine derivatives obtained in the above described Preparation Examples 1 to 21. (2) Bioassay (treatment under submerged condition)

A 1/15500-are porcelain pot was filled with the soil of a paddy field and seeds of Echinochloa crus-galli L., Cyperus difformis L., Rotala indica (Willd.) Koehne var. uligirosa (Miq.) Koehne., Monochoria vaginalis Presl var. plantaginea (Roxb.) Solms-Laub. and Scirpus juncoides Roxb. var Hotarui Ohwi were sown uniformly in the upper layer of the soil. And then the tubers of Cyperus serotinus Rottb. and Sagittaria pygmaea Miq. were planted in the soil, thereafter young rice plants of the second-leaf stage were transplanted.

When the weeds were germinated, a predetermined amount of a diluted solution of a herbicide prepared as reported in paragraph (1) hereinbefore was uniformly applied dropwise to the surface of the water and then the pot was kept in a intervals.

Table 5 shows the results obtained by the observation of the herbicidal effects and phytotoxicity to the rice plants at 20 days after treatment with the herbicide. The amount of the herbicide is given by the amount of the active ingredient per 10 ares. The phytotoxicity and the herbicidal effects were expressed as follows in terms of the respective dry matter weights.

| Rating of phytotoxicity | Phytotoxicity to the paddy rice plants (ratio to the untreated pot) |
| --- | --- |
| 0 | 100% |
| 1 | 95 to 99% |
| 2 | 90 to 94% |
| 3 | 80 to 89% |
| 4 | 60 to 79% |
| 5 | 50 to 69% |

| Rating of herbicidal effect | Herbicidal effect (ratio to the untreated pot) |
| --- | --- |
| 0 | 100% |
| 1 | 61 to 99% |
| 2 | 21 to 60% |
| 3 | 11 to 20% |
| 4 | 1 to 10% |
| 5 | 0% |

COMPARATIVE EXAMPLE

The same procedure as in Example 1 was undertaken except that the triaxine derivative in Example 1 prepared in Preparation Example 1 was replaced with 2-amino-4-($\alpha$-methylbenzyl amino)-5-trifluoromethyl-s-triazine expressed by the formula given below (specification of U.S. Pat. No. 3,816,419). The results are shown in Table 5.

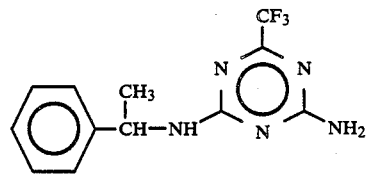

TABLE 5

| No. | Compound as effective component | Amount of herbicide (g/10 ares) | Herbicidal effect Echinochola crus-galli L. | Cyperus serotinus Rottb. | Scirpus juncoides Roxb. var Hotarui Ohwi | Cyperus difformis L. | Annual broadleaf weeds | Sagittaria pygmaea Miq. | Phytotoxicity to the paddy rice plants |
| --- | --- | --- | --- | --- | --- | --- | --- | --- | --- |
| Example 1 | Compound of Preparation Example 1 | 50 | 5 | 5 | 5 | 5 | 5 | 5 | 0 |
| | | 25 | 5 | 5 | 5 | 5 | 5 | 4 | 0 |
| Example 2 | Compound of Preparation Example 2 | 100 | 5 | 5 | 5 | 5 | 5 | 5 | 0 |
| | | 50 | 5 | 5 | 5 | 5 | 5 | 4 | 0 |
| | | 25 | 5 | 5 | 5 | 5 | 5 | 4 | 0 |
| Example 3 | Compound of Preparation Example 3 | 100 | 5 | 5 | 5 | 5 | 5 | 5 | 0 |
| | | 50 | 5 | 5 | 4 | 5 | 5 | 4 | 0 |
| Example 4 | Compound of Preparation Example 4 | 100 | 5 | 5 | 5 | 5 | 5 | 5 | 0 |
| | | 50 | 5 | 5 | 5 | 5 | 5 | 5 | 0 |
| | | 25 | 5 | 5 | 5 | 5 | 5 | 4 | 0 |
| Example 5 | Compound of Preparation Example 5 | 50 | 5 | 5 | 5 | 5 | 5 | 5 | 0 |
| | | 25 | 5 | 5 | 5 | 5 | 5 | 5 | 0 |
| Example 6 | Compound of Preparation Example 6 | 100 | 5 | 5 | 5 | 5 | 5 | 5 | 0 |
| | | 50 | 5 | 5 | 5 | 5 | 5 | 5 | 0 |
| | | 25 | 5 | 5 | 5 | 5 | 5 | 5 | 0 |
| Example 7 | Compound of Preparation Example 7 | 100 | 5 | 5 | 5 | 5 | 5 | 5 | 0 |
| | | 50 | 5 | 5 | 5 | 5 | 5 | 4 | 0 |
| | | 25 | 5 | 5 | 4 | 5 | 5 | 4 | 0 |
| Example 8 | Compound of Preparation Example 8 | 100 | 5 | 5 | 5 | 5 | 5 | 5 | 0 |
| | | 50 | 5 | 5 | 5 | 5 | 5 | 4 | 0 |
| | | 25 | 5 | 5 | 4 | 5 | 5 | 4 | 0 |
| Example 9 | Compound of Preparation Example 9 | 100 | 5 | 5 | 5 | 5 | 5 | 5 | 0 |
| | | 50 | 5 | 5 | 5 | 5 | 5 | 5 | 0 |
| | | 25 | 5 | 5 | 5 | 5 | 5 | 5 | 0 |
| Example 10 | Compound of Preparation Example 10 | 100 | 5 | 5 | 5 | 5 | 5 | 5 | 0 |
| | | 50 | 5 | 4 | 5 | 5 | 5 | 5 | 0 |
| | | 25 | 5 | 4 | 5 | 5 | 5 | 4 | 0 |
| Example 11 | Compound of Preparation Example 11 | 100 | 5 | 5 | 5 | 5 | 5 | 5 | 0 |
| | | 50 | 5 | 4 | 5 | 5 | 5 | 4 | 0 |
| | | 25 | 5 | 4 | 4 | 5 | 5 | 4 | 0 |
| Example 12 | Compound of Preparation Example 12 | 100 | 5 | 5 | 5 | 5 | 5 | 5 | 0 |
| | | 50 | 5 | 5 | 4 | 5 | 5 | 5 | 0 |
| | | 25 | 5 | 5 | 4 | 5 | 5 | 5 | 0 |
| Example 13 | Compound of Preparation Example 13 | 100 | 5 | 5 | 5 | 5 | 5 | 5 | 0 |
| | | 50 | 5 | 5 | 5 | 5 | 5 | 5 | 0 |
| | | 25 | 5 | 5 | 5 | 5 | 5 | 5 | 0 |
| Example 14 | Compound of Preparation Example 14 | 50 | 5 | 5 | 5 | 5 | 5 | 5 | 0 |
| | | 25 | 5 | 5 | 5 | 5 | 5 | 4 | 0 |
| Example 15 | Compound of Preparation Example 15 | 100 | 5 | 5 | 5 | 5 | 5 | 5 | 0 |
| | | 50 | 5 | 5 | 5 | 5 | 5 | 4 | 0 |
| | | 25 | 5 | 5 | 5 | 5 | 5 | 4 | 0 |
| Example 16 | Compound of Preparation Example 16 | 50 | 5 | 5 | 5 | 5 | 5 | 5 | 0 |
| | | 25 | 5 | 5 | 5 | 5 | 5 | 5 | 0 |
| Example 17 | Compound of Preparation Example 17 | 100 | 5 | 5 | 5 | 5 | 5 | 5 | 0 |
| | | 50 | 5 | 5 | 5 | 5 | 5 | 5 | 0 |
| | | 25 | 5 | 5 | 5 | 5 | 5 | 5 | 0 |
| Example 18 | Compound of Preparation Example 18 | 100 | 5 | 5 | 5 | 5 | 5 | 5 | 0 |
| | | 50 | 5 | 5 | 5 | 5 | 5 | 5 | 0 |
| | | 25 | 5 | 5 | 5 | 5 | 5 | 5 | 0 |
| Example 19 | Compound of | 100 | 5 | 5 | 5 | 5 | 5 | 5 | 0 |

TABLE 5-continued

| No. | Compound as effective component | Amount of herbicide (g/10 ares) | Echinochola crus-galli L. | Cyperus serotinus Rottb. | Scirpus juncoides Roxb. var Hotarui Ohwi | Cyperus difformis L. | Annual broadleaf weeds | Sagittaria pygmaea Miq. | Phytotoxicity to the paddy rice plants |
|---|---|---|---|---|---|---|---|---|---|
| | Preparation Example 19 | 50 | 5 | 5 | 5 | 5 | 5 | 5 | 0 |
| | | 25 | 5 | 5 | 5 | 5 | 5 | 5 | 0 |
| Example 20 | Compound of | 100 | 5 | 5 | 5 | 5 | 5 | 5 | 0 |
| | Preparation Example 20 | 50 | 5 | 5 | 5 | 5 | 5 | 5 | 0 |
| | | 25 | 5 | 5 | 5 | 5 | 5 | 5 | 0 |
| Example 21 | Compound of | 100 | 5 | 5 | 5 | 5 | 5 | 5 | 0 |
| | Preparation Example 21 | 50 | 5 | 5 | 5 | 5 | 5 | 5 | 0 |
| | | 25 | 5 | 5 | 5 | 5 | 5 | 5 | 0 |
| Comparative Example | | 100 | 5 | 1 | 2 | 5 | 5 | 1 | 5 |
| | | 50 | 4 | 0 | 0 | 5 | 5 | 0 | 3 |
| | | 25 | 1 | 0 | 0 | 2 | 5 | 0 | 1 |

POSSIBILITY OF INDUSTRIAL UTILIZATION

The novel triazine derivatives of the present invention are useful as a herbicide for paddy rice plants exhibiting greater effectiveness than known herbicides still with less injury of chemicals against the paddy rice plants. Moreover, they have a large width of the herbicidal spectrum exhitibing excellent herbicidal effects against various kinds of weeds with a coverage from annual weeds to perennial weeds.

We claim:

1. A triazine derivative represented by the formula

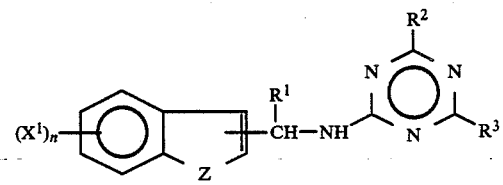

or by the formula

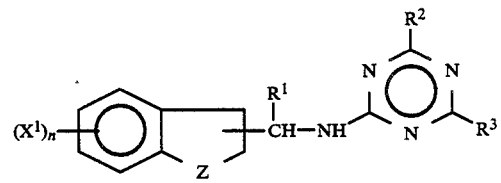

in the formulas, $X^1$ is a hydrogen atom, an alkyl group having 1 to 4 carbon atoms, an alkoxy group having 1 to 4 carbon atoms, an alkylthio group having 1 to 4 carbon atoms, a halogen atom, a halogen-substituted alkyl group having 1 to 4 carbon atoms, a halogen-substituted alkoxy group having 1 to 4 carbon atoms or a halogen-substituted alkylthio group having 1 to 4 carbon atoms, n is an integer of 1 to 4, Z is an oxygen atom or a sulfur atom, $R^1$ is an alkyl group having 1 to 4 carbon atoms, $R^2$ is a halogen-substituted alkyl group having 1 to 4 carbon atoms and $R^3$ is $NH_2$, $NHCOR^4$ or $N=CHR^5$ in which $R^4$ is a hydrogen atom, an alkyl group having 1 to 4 carbon atoms, a substituted alkyl group having 1 to 4 carbon atoms, a cycloalkyl group having 3 to 6 carbon atoms or an alkenyl group having 2 to 5 carbon atoms and $R^5$ is an alkyl group having 1 to 4 carbon atoms, an alkoxy group having 1 to 4 carbon atoms or an alkylamino group having 1 to 4 carbon atoms.

2. The triazine derivative of claim 1 wherein $X^1$ is hydrogen, the alkyl group having 1 to 4 carbon atoms or the alkoxy group having 1 to 4 carbon atoms.

3. The triazine derivative of claim 2 wherein $R^3$ is $NH_2$.

4. The triazine derivative of claim 2 wherein $R^3$ is $NHCOR^4$.

5. The triazine derivative of claim 2 wherein $R^3$ is $N=CHR^5$.

6. The triazine derivative of claim 1, wherein $X^1$ is the alkylthio group having 1 to 4 carbon atoms or the halogen substituted alkylthio group having 1 to 4 carbon atoms.

7. The triazine derivative of claim 1, wherein $X^1$ is the halogen atom, the halogen substituted alkyl group having 1 to 4 carbon atoms or the halogen substituted alkoxy group having 1 to 4 carbon atoms.

8. The triazine derivative of claim 1 of the formula

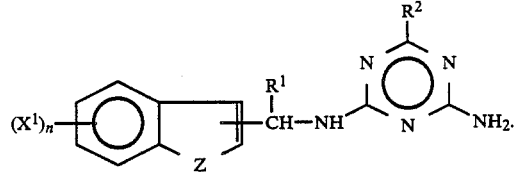

9. The triazine derivative of claim 1 of the formula

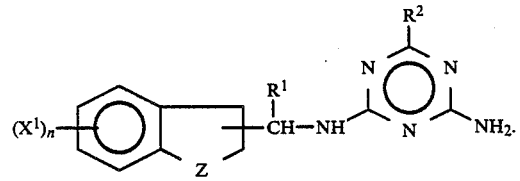

10. The triazine derivative of claim 1 of the formula

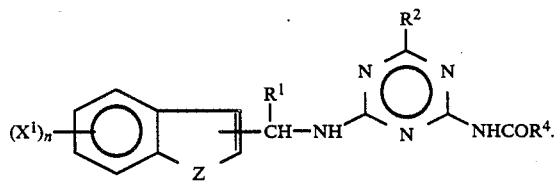

11. The triazine derivative of claim 1 of the formula

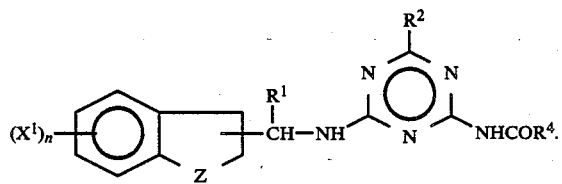

12. The triazine derivative of claim 1 of the formula

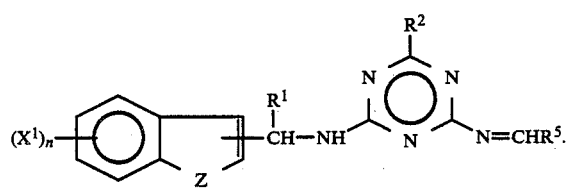

13. The triazine derivative of claim 1 of the formula

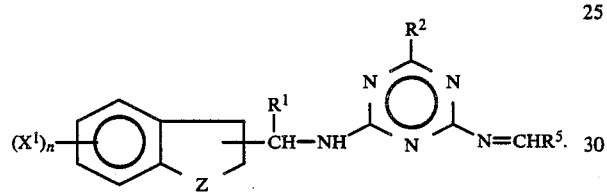

14. The triazine derivative of claim 1 of the formula

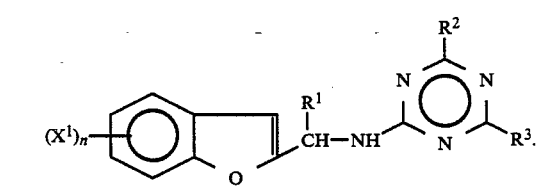

15. The triazine derivative of claim 1 of the formula

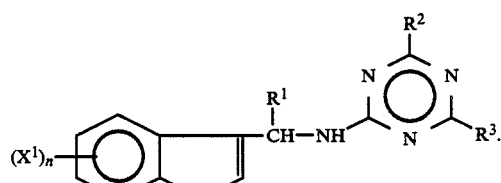

16. The triazine derivative of claim 1 of the formula

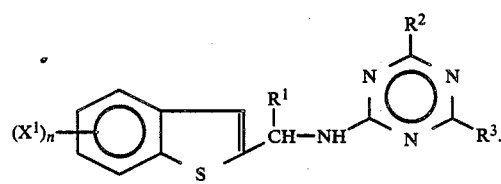

17. The triazine derivative of claim 1 of the formula

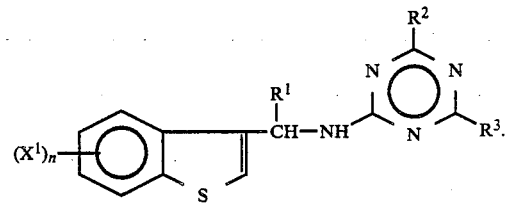

18. The triazine derivative of claim 1 of the formula

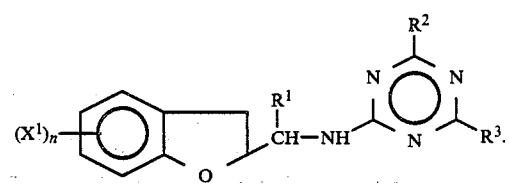

19. The triazine derivative of claim 1 of the formula

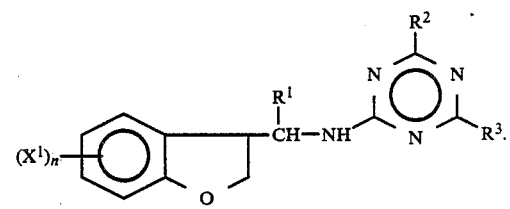

20. The triazine derivative of claim 1 of the formula

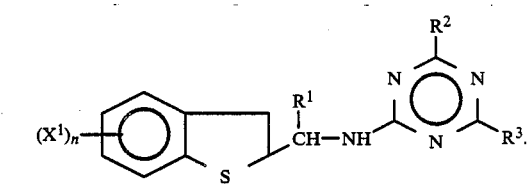

21. The triazine derivative of claim 1 of the formula

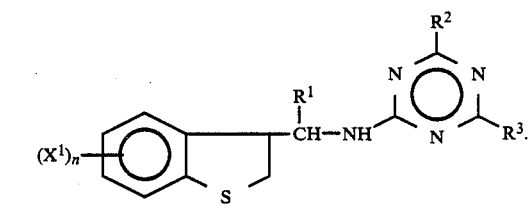

22. The triazine derivative of claim 1 of the formula

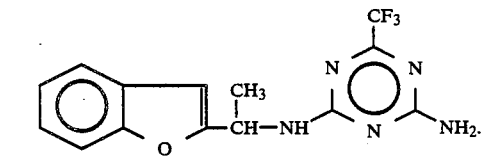

23. The triazine derivative of claim 1 of the formula

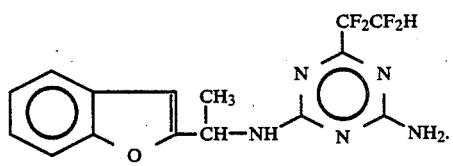

24. The triazine derivative of claim 1 of the formula

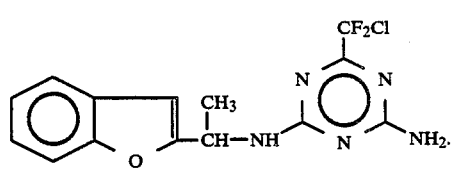

25. The triazine derivative of claim 1 of the formula

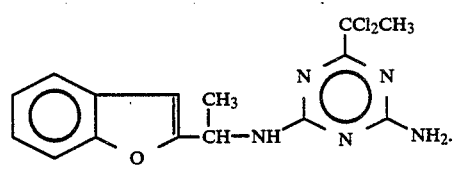

26. The triazine derivative of claim 1 of the formula

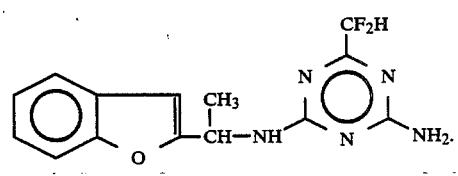

27. The triazine derivative of claim 1 of the formula

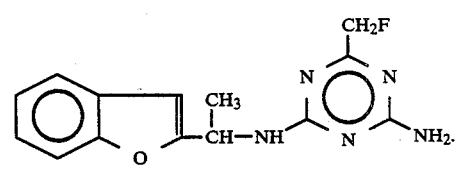

28. The triazine derivative of claim 1 of the formula

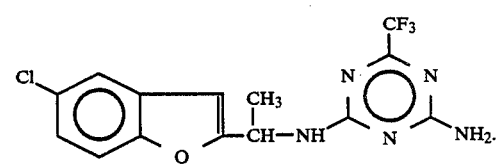

29. The triazine derivative of claim 1 of the formula

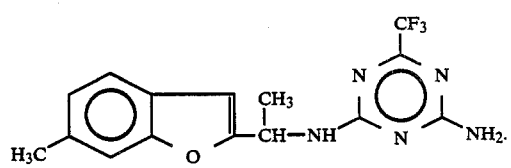

30. The triazine derivative of claim 1 of the formula

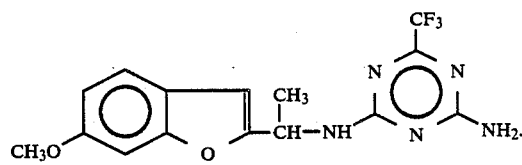

31. The triazine derivative of claim 1 of the formula

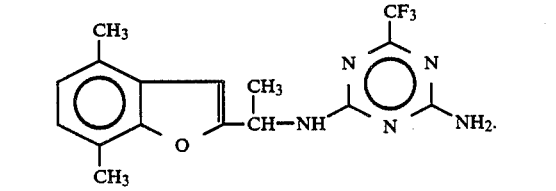

32. The triazine derivative of claim 1 of the formula

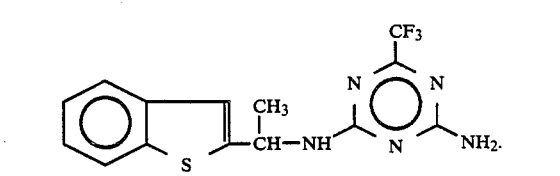

33. The triazine derivative of claim 1 of the formula

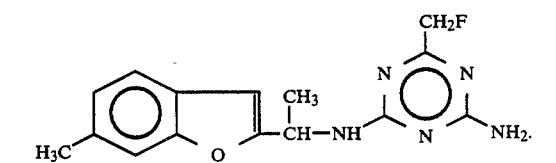

34. The triazine derivative of claim 1 of the formula

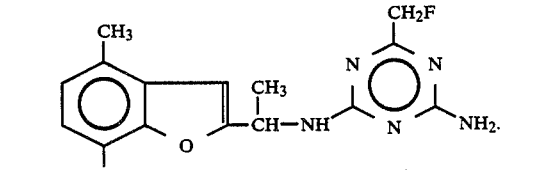

35. The triazine derivative of claim 1 of the formula

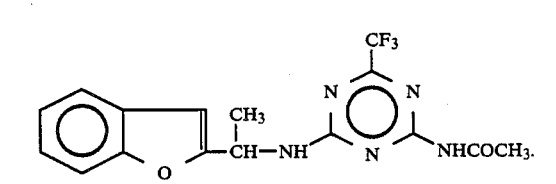

36. The triazine derivative of claim 1 of the formula

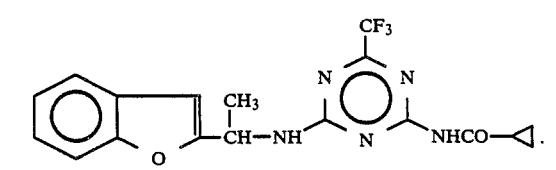

37. The triazine derivative of claim 1 of the formula

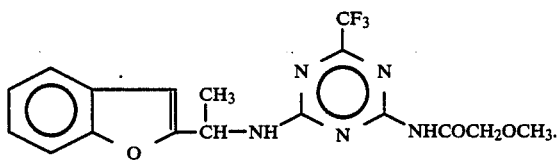

38. The triazine derivative of claim 1 of the formula

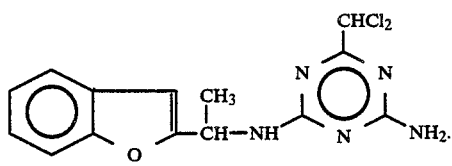

39. The triazine derivative of claim 1 of the formula

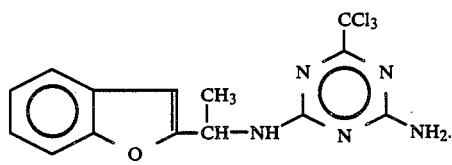

40. The triazine derivative of claim 1 of the formula

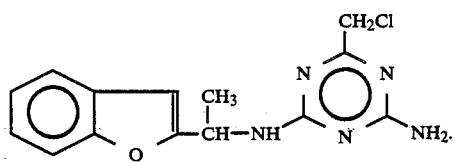

41. The triazine derivative of claim 1 of the formula

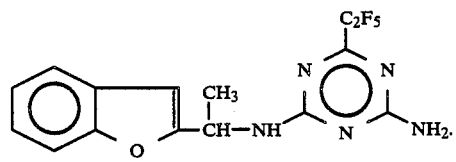

42. The triazine derivative of claim 1 of the formula

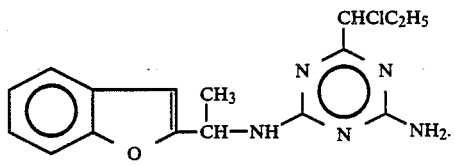

43. An herbicidal composition comprising an herbicidally effective amount of a triazine derivative in an herbicidally acceptable carrier, said triazine derivative being represented by the formula

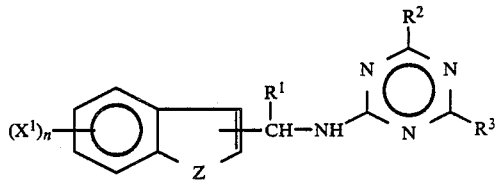

or by the formula

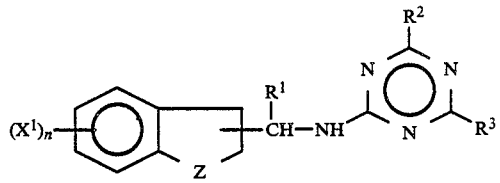

in the formulas, $X^1$ is a hydrogen atom, an alkyl group having 1 to 4 carbon atoms, an alkoxy group having 1 to 4 carbon atoms, an alkylthio group having 1 to 4 carbon atoms, a halogen atom, a halogen-substituted alkyl group having 1 to 4 carbon atoms, a halogen-substituted alkoxy group having 1 to 4 carbon atoms or a halogen-substituted alkylthio group having 1 to 4 carbon atoms, n is an integer of 1 to 4, Z is an oxygen atom or a sulfur atom, $R^1$ is an alkyl group having 1 to 4 carbon atoms, $R^2$ is a halogen-substituted alkyl group having 1 to 4 carbon atoms and $R^3$ is $NH_2$, $NHCOR^4$ or $N=CHR^5$ in which $R^4$ is a hydrogen atom, an alkyl group having 1 to 4 carbon atoms, a substituted alkyl group having 1 to 4 carbon atoms, a cycloalkyl group having 3 to 6 carbon atoms or an alkenyl group having 2 to 5 carbon atoms and $R^5$ is an alkyl group having 1 to 4 carbon atoms, an alkoxy group having 1 to 4 carbon atoms or an alkylamino group having 1 to 4 carbon atoms.

* * * * *